US010898413B2

United States Patent
Elia et al.

(10) Patent No.: US 10,898,413 B2
(45) Date of Patent: Jan. 26, 2021

(54) SYSTEMS AND METHODS FOR DYNAMIC CONTROL OF ENTERAL FEEDING ACCORDING TO ENERGY EXPENDITURE

(71) Applicant: ART Medical Ltd., Netanya (IL)

(72) Inventors: Liron Elia, Kiryat-Ata (IL); Gavriel J. Iddan, Haifa (IL)

(73) Assignee: ART MEDICAL Ltd., Netanya (IL)

( * ) Notice: Subject to any disclaimer, the term of this patent is extended or adjusted under 35 U.S.C. 154(b) by 0 days.

(21) Appl. No.: 16/500,141

(22) PCT Filed: Nov. 21, 2017

(86) PCT No.: PCT/IL2017/051271
§ 371 (c)(1),
(2) Date: Oct. 2, 2019

(87) PCT Pub. No.: WO2018/185738
PCT Pub. Date: Oct. 11, 2018

(65) Prior Publication Data
US 2020/0222286 A1    Jul. 16, 2020

Related U.S. Application Data

(60) Provisional application No. 62/480,473, filed on Apr. 2, 2017.

(51) Int. Cl.
*G16H 10/60* (2018.01)
*A61J 15/00* (2006.01)
(Continued)

(52) U.S. Cl.
CPC ......... *A61J 15/0084* (2015.05); *A61B 5/0833* (2013.01); *A61B 5/0836* (2013.01);
(Continued)

(58) Field of Classification Search
CPC .. A61J 15/0084; A61J 15/0092; G16H 10/60; G16H 40/63; G16H 20/60; A61B 5/0833; A61B 5/0836; A61B 5/208
(Continued)

(56) References Cited

U.S. PATENT DOCUMENTS

| 3,935,971 A * | 2/1976 | Papoff | F04B 43/1292 222/134 |
| 2007/0112323 A1* | 5/2007 | Daly | A61M 39/08 604/411 |
| 2016/0058673 A1* | 3/2016 | Francis | G16H 20/17 604/65 |

FOREIGN PATENT DOCUMENTS

WO   WO 2018/185738   10/2018

OTHER PUBLICATIONS

International Preliminary Report on Patentability dated Jul. 15, 2019 From the International Preliminary Examining Authority Re. Application No. PCT/IL2017/051271. (40 Pages).
(Continued)

*Primary Examiner* — Michael Tomaszewski

(57) ABSTRACT

A computer-implemented method of adjusting enteral feeding of a patient by an enteral feeding controller, comprising: computing an estimate of energy expenditure of the patient based on oxygen measurements and carbon dioxide measurements of the patient, computing a target composition and target feeding rate for the enteral feeding according to the computed estimate of energy expenditure, when the target composition and target feeding rate differ from a current enteral feeding composition and feeding rate by a requirement, generating instructions for adjustment, by an enteral feeding controller, of the rate of delivery of the enteral feeding according to the target composition, wherein the receiving the oxygen measurement, receiving the carbon dioxide measurement, and computing the estimate of energy
(Continued)

expenditure are performing iteratively for every first time interval, and the generating instructions for adjustment are performed for a second time interval that is larger than the first time interval.

21 Claims, 16 Drawing Sheets

(51) Int. Cl.
  *G16H 40/63* (2018.01)
  *G16H 20/60* (2018.01)
  *A61B 5/083* (2006.01)
  *A61B 5/20* (2006.01)

(52) U.S. Cl.
  CPC ............ *A61B 5/208* (2013.01); *G16H 10/60* (2018.01); *G16H 20/60* (2018.01); *G16H 40/63* (2018.01); *A61J 15/0092* (2013.01)

(58) Field of Classification Search
  USPC .......................................... 705/2–3
  See application file for complete search history.

(56) References Cited

OTHER PUBLICATIONS

International Search Report and the Written Opinion dated Feb. 26, 2018 From the International Searching Authority Re. Application No. PCT/IL2017/051271. (20 Pages).
Written Opinion dated Mar. 6, 2019 From the International Preliminary Examining Authority Re. Application No. PCT/IL2017/051271. (16 Pages).
Wikipedia "Indirect Calorimetry", Wikipedia, the Free Encyclopedia, XP055450201, Retrieved From the Internet, 3 P., Aug. 28, 2016. Scientific Background.

* cited by examiner

JEVITY® 1.5 CAL

Complete, Balanced Nutrition® With Fiber and NutraFlora® scFOS®

JEVITY 1.5 CAL is a calorically dense formula with a unique fiber blend that provides Complete, Balanced Nutrition®. For tube feeding. For supplemental or sole-source nutrition. May be used for oral feeding of patients with altered taste perception. Use under medical supervision.

| Unflavored Liquid |
| 1500 mL (1.6 QT) |

NUTRIENT DATA

|  | Amount per Serving | % DV | % RDI† |
|---|---|---|---|
| Protein, g | 95.7 | | |
| Fat, g | 74.7 | | |
| Carbohydrate, g | 323.0 | | |
|    Dietary Fiber, g | 33.0† | | |
| L-Carnitine, mg | 225 | | |
| Taurine, mg | 225 | | |
| Water, g/mL/cc | 1140 | | |
| Calories | 2250 | | |

Set patient's condition 1  select if the patient has any of the following conditions — 614

| Maintenance | Stressed/MICU | Trauma/General Surgery |
| Trauma/ICU | Burns | Cancer |
| | | Obesity BMI >29.9 |

2  Patient weight — 612

50 kg 20  30  40  50  60  70  80  90  100  110  120  130

REE: 1500 cal + 50gr protein ← 616

Skip    Continue

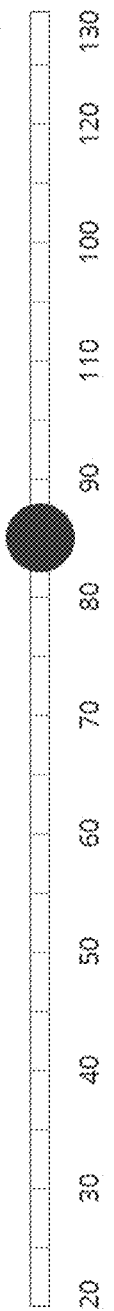

FIG. 6D

Select Formula    ● Continuous    ○ Intermittent

Optimal Formula

| Osmolite | 100% cal / 85% Protein |
| 75 cc/h | |

Jevity+ — 100% cal / 80% Protein — 80 cc/h

Perative — 100% cal / 78% Protein — 85 cc/h

Show all results (5)

Standard Formula

Pulmocare — 90% cal / 90% Protein — 75 cc/h

Osmolite — 83% cal / 88% Protein — 75 cc/h

Nepro LP — 80% cal / 90% Protein — 80 cc/h

Show all results (7)

618

Skip

FIG. 6E select and add Protein

Osmolite 75 cc/h    100% cal    85% Protein

For 100% protein, Select type:

| Protein formula name | Recommended add |
|---|---|
| THEWHEY | 60 gr > |
| Gold Standard 100% Whey | 45 gr > |
| ISO100 | 50 gr > |
| NITRO-TECH | 60 gr > |
| Gold Standard 100% Casein | 30 gr > |

Continue without adding

FIG. 6F

Select and add Protein

Osmolite 75 cc/h     100 % cal     85 % Protein

For 100% protein, Select type:

| Protein formula name | Recommended add | |
|---|---|---|
| THEWHEY | 60 gr | > |
| Gold Standard 100% Whey<br>Optimum Nutrition<br>Muscle Building Whey Protein Powder | 45 gr | < Add 45 gr and continue |
| ISO100 | 50 gr | > |
| NITRO-TECH | 60 gr | Continue without adding |

FIG. 6G

Select Formula  ● Continuous  ○ Intermittent  Manual Options

Average Feeding

| Pulmocare | 90% Cal | 85% Protein |
| 75 cc/h | | |

| Osmolite | 83% Cal | 88% Protein |
| 75 cc/h | | |

| Nepro LP | 80% Cal | 90% Protein |
| 80 cc/h | | |

Show all results (7)

Manual Feeding

Select Type

| Osmolite | Jevity+ | Perative |
| Nepro LP | Pulmocare | |

Select other type

Select Quantity (cc/h)

| 40 | 45 | 50 | 55 | 60 |
| 65 | 70 | 75 | 80 | 90 |

Choose other quantity

620

Skip

FIG. 6H  ● Continuous  ○ Intermittent   Manual Option

Select Formula

Average Feeding

Pulmocare — 90% cal / 85% Protein
75 cc/h

Osmolite — 83% cal / 88% Protein
75 cc/h

Nepro LP — 80% cal / 90% Protein
80 cc/h

Show all results (7)

Manual Feeding

Select Type
Osmolite | Jevity+ | Perative
Nepro LP | Pulmocare

Select other type

Select Quantity (cc/h)
40 | 45 | 50 | 55 | 60
65 | 70 | 75 | 80 | 90

Choose other quantity
Type Quantity — 622

OK    Skip

FIG. 6I

Select Formula  ◯ Continuous  ⦿ Intermittent

Intermittent feeding

Frequency: | 2 Hours | 3 Hours | 4 Hours | 6 Hours
Duration: | 1 Hours | 2 Hours Taper up: | 5 min | 10 min | 15 min | 20 min
Taper down: | 5 min | 10 min | 15 min | 20 min

00:00  04:00  08:00  12:00  16:00  20:00  24:00

Intermittent button selected

Submit and calculate

SYSTEMS AND METHODS FOR DYNAMIC CONTROL OF ENTERAL FEEDING ACCORDING TO ENERGY EXPENDITURE

RELATED APPLICATIONS

This application is a National Phase of PCT Patent Application No. PCT/IL2017/051271 having International filing date of Nov. 21, 2017, which claims the benefit of priority under 35 USC § 119(e) of U.S. Provisional Patent Application No. 62/480,473 filed on Apr. 2, 2017. The contents of the above applications are all incorporated by reference as if fully set forth herein in their entirety.

BACKGROUND

The present invention, in some embodiments thereof, relates to enteral feeding systems and, more specifically, but not exclusively, systems and methods for control of enteral feeding.

Patients requiring enteral feeding (i.e., feeding via a tube inserted into the stomach) include, for example, babies, patients in the intensive care unit (ICU) which might be sedated and/or intubated, and patients otherwise unable to swallow or ingest food in the normal manner. The tube is inserted into the stomach (or duodenum, or jejunum, or other locations in the digestive track) via the nose, the mouth, or a surgically created opening. Recent research and practice indicated that correct patient enteral feeding is a crucial element in patient survival rate and recovery. Unfortunately in many cases the feed rate and composition is carried out when the patient enters the unit and updates are rare if at all. Systems and methods for improving patient enteral feeding are long sought after.

SUMMARY

According to a first aspect, a computer-implemented method of adjusting enteral feeding of a patient by an enteral feeding controller, comprises: receiving carbon dioxide measurements outputted by a carbon dioxide sensor that senses at least one of inspiration and expiration of the patient, receiving an oxygen measurement outputted by an oxygen sensor that senses at least one of inspiration and expiration of the patient, computing an estimate of energy expenditure of the patient based on the oxygen measurement and the carbon dioxide measurement, computing a target composition and target feeding rate for the enteral feeding according to the computed estimate of energy expenditure, when the target composition and target feeding rate differ from a current enteral feeding composition and feeding rate by a requirement, generating instructions for adjustment, by an enteral feeding controller, of the rate of delivery of the enteral feeding according to the target composition, wherein the receiving the oxygen measurement, receiving the carbon dioxide measurement, and computing the estimate of energy expenditure are performing iteratively for every first time interval, and the generating instructions for adjustment are performed for a second time interval that is larger than the first time interval.

According to a second aspect, a system for adjusting enteral feeding of a patient by an enteral feeding controller, comprises: a non-transitory memory having stored there a code for execution by at least one hardware processor of a computing system, the code comprising: code for receiving carbon dioxide measurements outputted by a carbon dioxide sensor that senses at least one of inspiration and expiration of the patient, code for receiving an oxygen measurement outputted by an oxygen sensor that senses at least one of inspiration and expiration of the patient, code for computing an estimate of energy expenditure of the patient based on the oxygen measurement and the carbon dioxide measurement, code for computing a target composition and target feeding rate for the enteral feeding according to the computed estimate of energy expenditure, code for when the target composition and target feeding rate differ from a current enteral feeding composition and feeding rate by a requirement, generating instructions for adjustment, by an enteral feeding controller, of the rate of delivery of the enteral feeding according to the target composition, wherein the receiving the oxygen measurement, receiving the carbon dioxide measurement, and computing the estimate of energy expenditure are performing iteratively for every first time interval, and the generating instructions for adjustment are performed for a second time interval that is larger than the first time interval.

According to a third aspect, a computer program product for adjusting enteral feeding of a patient by an enteral feeding controller, comprises: a non-transitory memory having stored there a code for execution by at least one hardware processor of a computing system, the code comprising: instructions for receiving carbon dioxide measurements outputted by a carbon dioxide sensor that senses at least one of inspiration and expiration of the patient, instructions for receiving an oxygen measurement outputted by an oxygen sensor that senses at least one of inspiration and expiration of the patient, instructions for computing an estimate of energy expenditure of the patient based on the oxygen measurement and the carbon dioxide measurement, instructions for computing a target composition and target feeding rate for the enteral feeding according to the computed estimate of energy expenditure, instructions for when the target composition and target feeding rate differ from a current enteral feeding composition and feeding rate by a requirement, generating instructions for adjustment, by an enteral feeding controller, of the rate of delivery of the enteral feeding according to the target composition, wherein the receiving the oxygen measurement, receiving the carbon dioxide measurement, and computing the estimate of energy expenditure are performing iteratively for every first time interval, and the generating instructions for adjustment are performed for a second time interval that is larger than the first time interval.

According to a fourth aspect, a computer-implemented method of adjusting enteral feeding of a patient by an enteral feeding controller, comprises: receiving a carbon dioxide measurement outputted by a carbon dioxide sensor that senses inspiration and expiration of the patient, receiving an oxygen measurement outputted by an oxygen sensor that senses inspiration and expiration of the patient, computing an estimate of energy expenditure of the patient based on the oxygen measurement and the carbon dioxide measurement, computing a target composition for the enteral feeding according to the computed estimate of energy expenditure, computing an amount of supplemental protein to meet enteral feeding requirements of the patient based on the computed energy expenditure, the amount of supplemental protein computed based on the target composition in view of available formulation stored in a database storing records of different compositions of enteral feeding formulation, and generating instructions for adjustment, by an enteral feeding controller, of the rate of delivery of the amount of supplemental protein and the target composition, wherein the receiving the oxygen measurement, receiving the carbon dioxide measurement, and computing the estimate of energy expenditure are performing iteratively for every first time interval, and the generating instructions for adjustment are performed for a second time interval that is larger than the first time interval.

The systems, methods, apparatus, and/or code instructions described herein relate to the technical problem of control of enteral feeding of a patient. Design and/or selection of an appropriate enteral feeding regime, which includes the feeding rate (e.g., calories per unit of time) and/or composition of the enteral feeding (e.g., mix of carbohydrates, protein, fat and/or other nutrients) affects patient survival and recovery.

According to standard practice (e.g., when the patient enters the intensive care unit (ICU)) a feeding plan (e.g., formulation, rate, pattern of delivery) is manually assigned, for example, by a healthcare provider and/or nutritionist currently calculating nutritional goal according to Harris Benedict formula or alike (which is generally not accurate and/or performed only one time for the patient) and not according to dynamic- and changing nutritional goal as patient status continuously changes. The feeding plan is selected according to the specific situation of the patient, according to specification(s) of the variations of feedings available from different vendors, and the currently stocked supply. The feeding plan is manually designed based on dietician and/or nutritionist knowhow and/or known recommended formulas, team leader experience (e.g., head of ICU), and/or patient specific requirement as prescribed by the current attending physical. The manual method, which is based on subjective inputs from one or more people, results in sub-optimal planning for the specific patient that does not precisely match the patient's current metabolism.

In contrast to the standard manual practice, the systems, methods, apparatus, and/or code instructions described herein without the need for a "man in the loop" dynamically determine objectively the patient condition in terms of energy expenditure, and dynamically adjust the enteral feeding accordingly.

The systems, methods, apparatus, and/or code instructions described herein may further relate to the technical problem of adjusting patient enteral feeding according to dynamic patient conditions. For example, in the ICU, the patient condition may change rapidly, and many variations may be experienced. For example, as the patient recovers, undergoes changes in treatments, and experiences new infections and new medical conditions. The current practice of manual methods, which are based on manual calculations of the most suitable enteral feeding regime at a certain point in time, are unable to adequately adapt to rapidly changing patient conditions. For example, continuous checking the patient, analyzing the patient condition, replacing different feedings, and updating of the feeding regiment are impractical and cannot be manually performed to keep up with the changing condition of the patient.

When the patient feeding is manually determined and manually performed, the determination of how to feed the patient is based on outdated data which do not reflect the actual current state of the patient. Therefore, the manually determined feeding plan is not suitable for the current state of the patient. In contrast, the systems, methods, and/or code instructions described herein obtain an accurate current state of the patient, and dynamically select and/or adjust the feeding regimen (e.g., composition, rate) for the patient based on the current state of the patient. The feeding regimen is quickly adjusted to reflect changes in the current state of the patient, which cannot be performed by manual methods that are based on outdated states of the patient and not the current state of the patient.

Moreover, healthcare providers are unable to continuously monitor patient caloric consumption, which may lead to sub-optimal feeding of the patient, for example, underfeeding of the patient which may lead to inadequate caloric and/or protein and or nutrition intake with adverse effects on recovery and/or survival, and/or overfeeding (it is noted that overfeeding may be an indication of poor stomach pyloric discharge or other gastric blockage that require special treatment) of the patient which may lead to reflux and associated risks thereof (e.g., aspiration pneumonia).

The systems, methods, apparatus, and/or code instructions described herein do not simply perform automation of a manual procedure, but perform additional automated features which cannot be performed manually by a human using pencil and/or paper. For example, combination of food sources may be controlled each at a respective rate, for example, a high protein food source and a standard food source. In another example, the computations are performed in real-time (i.e., over short intervals) based on sensors measuring oxygen, carbon dioxide, and/or nitrogen flows of the patient, which cannot be performed manually. In yet another example, the target composition and target feeding rate are computed according to the computed energy expenditure and evaluated to determine whether a significant change has occurred from the current feeding. Instructions to adjust the feeding controller are automatically generated when the significant change occurs, to change the composition and/or feeding rate. The process is iterated at short time intervals to quickly identify changes in the energy expenditure of the patient and adjust feeding accordingly, which cannot be performed manually. In yet another example, the feeding is adjusted in real-time to prevent or reduce reflux based on estimated GRV. In another example, a prediction of future feeding needs is made based on historical measurements of feeding performance.

The GUI associated with the systems, apparatus, methods and/or code instructions described herein generates a new user experience, one that is different than manually trying to select feeding formulas and select the feeding rate. For example, the GUI guides the user through the process of selecting the feeding formulas and the feeding rate, as described herein. The GUI visually presents different suitable and available feeding formulas for the user to pick from. The GUI guides the user to select supplemental protein from suitable and available feeding formula. The GUI presents to the user suitable options based on the automatically computed resting energy expenditure of the patient, which aids the user in making correct feeding selections. The GUI may present a graphical representation of selected intermittent feeding parameters, to help visualize how the feeding will take placing during the upcoming time interval.

The systems, methods, and/or code instructions described herein do not simply display information using a GUI. The systems, methods, and/or code instructions described herein may be based on a specific, structured GUI, which is paired with a prescribed functionality directly related to the GUI s structure that is addressed to and resolves the specifically identified technical problem.

When the features related to by the systems, methods, apparatus, and/or code instructions described herein are taken as a whole, the combination of the features amounts to significantly more than a simple mathematical calculation of computing the estimated energy expenditure rate (e.g., the resting energy expenditure rate). The systems, methods, apparatus, and/or code instructions described herein do not merely relate to mathematical computations (e.g., equations), but relate to the particular data collected, stored, and the way the data is collected by sensors, and how instructions for adjustment of the enteral feeding device (e.g., pump, valve) are automatically generated.

In a further implementation form of the first, second, and third aspects, the method further comprises and/or the system further includes code for and/or the computer program product includes additional instructions for performing an analysis of real-time patient vial sign measurements collected from an electronic medical record of the patient to determine whether the patient is at rest, wherein the energy expenditure of the patient is computed when the patient is determined to be at rest.

In a further implementation form of the first, second, and third aspects, the second time interval is about 20 minutes or less.

In a further implementation form of the first, second, and third aspects, the instructions for adjustment include a first feeding interval associated with the rate of delivery of the enteral feeding, and second non-feeding interval during which no enteral feeding is delivered, wherein the first and second intervals are iterated.

In a further implementation form of the first, second, and third aspects, the target feeding rate is calculated based on carbon dioxide measurements alone when oxygen measurements are not available, and an estimated value for a respiratory quotient (RQ).

In a further implementation form of the first, second, and third aspects, the method further comprises and/or the system further includes code for and/or the computer program product includes additional instructions for receiving a nitrogen measurement outputted by a nitrogen sensor associated with a urine output collection device that collects urine outputted by the patient, and wherein the estimate of energy expenditure is further computed according to the nitrogen measurement.

In a further implementation form of the first, second, and third aspects, the method further comprises and/or the system further includes code for and/or the computer program product includes additional instructions for computing an amount of supplemental protein to meet enteral feeding requirements of the patient based on the computed energy expenditure, the amount of supplemental protein computed based on the target composition in view of available formulation stored in a database storing records of different compositions of enteral feeding formulation, wherein the supplemental protein when added to a selected available formulation does not significantly affect a computed caloric and/or volumetric feed rate of the available formulation to trigger a re-computation of the feeding rate of the available formulation.

In a further implementation form of the first, second, and third aspects, the method further comprises and/or the system further includes code for and/or the computer program product includes additional instructions for matching the computed target composition to at least one record of an available formulation stored in a database storing records of different compositions of enteral feeding formulation, wherein the instructions for adjustment are generated based on the matched at least one record.

In a further implementation form of the first, second, and third aspects, the method further comprises and/or the system further includes code for and/or the computer program product includes additional instructions for, when at least one record is matched to the target composition, presenting on a display the at least one record, and receiving via a user interface a selection of a certain record from the presented at least one record, wherein the instructions for adjustment are generated according to the selected certain record.

In a further implementation form of the first, second, and third aspects, the method further comprises and/or the system further includes code for and/or the computer program product includes additional instructions for computing a score indicative of similarity between each respective record and the target composition, and presenting the score in association with each respective record.

In a further implementation form of the first, second, and third aspects, the method further comprises and/or the system further includes code for and/or the computer program product includes additional instructions for when no records are matched to the target composition, independently matching a plurality of component sets of the target composition to respective a plurality of records, wherein each of a plurality of instructions for adjustment is generated according to a respective matched record of the plurality of records.

In a further implementation form of the first, second, and third aspects, a first set of components denotes arbitrary components matched to a first formulation, and a second set of components denotes a pure protein component matched to a second formulation, wherein a first set of instructions is generated for enteral feeding of the first formulation at a first rate, and a second set of instructions is generated for enteral feeding of the second formulation at a second rate.

In a further implementation form of the first, second, and third aspects, the target composition is computed based on an aggregation of data collected from a plurality of sampled individuals, wherein the target composition is computed according to a likelihood of obtaining a positive outcome.

In a further implementation form of the first, second, and third aspects, the generated instructions include a first set of instructions for delivery of a first enteral feeding formulation at a first rate, and a second set of instructions for delivery of a second enteral feeding formulation at a second rate, wherein the first set of instructions and the second set of instructions control a feed selecting mechanism that selects between a first tube that delivers the first enteral feeding formulation at the first rate and a second tube that delivers the second enteral feeding formulation at the second rate, wherein the first tube and the second tube connect into a combined tube that provides enteral feeding of the patient.

In a further implementation form of the first, second, and third aspects, the estimate of energy expenditure comprises an estimate of caloric expenditure of the patient, and wherein the enteral feeding controller dynamically adjusts the feeding rate to deliver calories to the patient according to the estimate of caloric expenditure.

In a further implementation form of the first, second, and third aspects, the estimate of energy expenditure is dynamically computed as a rate of energy expenditure for a pre-defined time duration during which the oxygen and carbon dioxide measurements are obtained, and wherein the feeding rate provided by the enteral feeding controller is dynamically adjusted to match the rate of energy expenditure within a tolerance requirement.

In a further implementation form of the first, second, and third aspects, the generated instructions define a feeding rate set below a reflux feeding level estimated to trigger reflux of the enteral feeding by the patient.

In a further implementation form of the first, second, and third aspects, the reflux feeding level is computed according to the net food portion of an estimated gastro residual volume (GRV), computed based on weight, volume, and specific gravity of the enteral feeding formulation delivered by the enteral feeding controller.

In a further implementation form of the first, second, and third aspects, the reflux feeding level is further computed according to historical feeding performance of the target individual.

In a further implementation form of the first, second, and third aspects, the target composition and target feeding rate include a volume of water.

In a further implementation form of the first, second, and third aspects, the method further comprises and/or the system further includes code for and/or the computer program product includes additional instructions for presenting on a display within a graphical user interface (GUI), at least one of: current computed energy expenditure, a trend based on history of the computed energy expenditure, current feeding rate delivered by the enteral feeding controller, and computed composition of the enteral feeding being delivered by the enteral feeding controller.

In a further implementation form of the first, second, and third aspects, the estimate of energy expenditure is computed based on a Weir or corresponding equations, and based on metabolic rate estimated from oxygen consumption computed based on the oxygen measurement and carbon dioxide production computed based on the carbon dioxide measurement.

In a further implementation form of the first, second, and third aspects, the method further comprises and/or the system further includes code for and/or the computer program product includes additional instructions for setting an initial feeding rate by the enteral feeding controller independently of the oxygen and carbon dioxide measurement, computing an mismatch between the computed estimate of energy expenditure and the initial feeding rate state, wherein the generated instructions include instructions for adjusting the initial feeding rate of the enteral feeding controller according to the computed mismatch.

In a further implementation form of the first, second, and third aspects, the estimate of energy expenditure comprises a prediction of future energy expenditure computed by machine learning code instructions trained according to previously observed patterns.

In a further implementation form of the first, second, and third aspects, the rate of delivery of the enteral feeding is further computed according to historical feeding performance of the patient indications.

In a further implementation form of the first, second, and third aspects, the carbon dioxide sensor is mounted on a ventilation tube ventilating the patient.

In a further implementation form of the fourth aspect, the amount of supplemental protein is computed for adding each of the available formulations for reaching about 100% of protein requirements of the computed target composition for the enteral feeding.

In a further implementation form of the fourth aspect, the method further comprises performing an analysis of real-time patient vial sign measurements collected from an electronic medical record of the patient to determine whether the patient is at rest, wherein the energy expenditure of the patient is computed when the patient is determined to be at rest.

In a further implementation form of the fourth aspect, the method further comprises setting a clinical state of the patient, wherein the target feeding composition is computed according to the clinical state of the patient.

In a further implementation form of the fourth aspect, the clinical state of the patient is selected from the group comprising: maintenance, stressed/MICU, trauma/general surgery, trauma/ICU, burn(s), cancer, obesity (e.g., body mass index (BMI)>29.9).

In a further implementation form of the fourth aspect, the method further comprises setting a weight of the patient, wherein the target feeding composition is computed according to the weight of the patient.

In a further implementation form of the fourth aspect, the method further comprises presenting on a display within a graphical user interface (GUI), an indication of a computed state of whether the patient is rested or un-rested, when the patient is determined as rested presenting an indication of the computed estimate of energy expenditure within the GUI, receiving via the GUI a setting of a patient weight, and a selection from a plurality of icons each denoting a respective clinical state of the patient, receiving via the GUI a selection of one icon indicative of one of the available formulation from a plurality of available formulations stored in the database and presented within the GUI based on respective icons, receiving via the GUI a selection of one icon indicative of one available supplemental protein formulation satisfying the amount of supplemental protein from a plurality of available formulations satisfying the amount of supplemental protein stored in a database storing records of different compositions of supplemental protein, and presented within the GUI based on respective icons, wherein the instructions for adjustment are generated according to the selections received via the GUI.

In a further implementation form of the fourth aspect, the method further comprises receiving, via the GUI, a selection of: an icon indicative of intermittent feeding, an icon indicative of a number of hours of a frequency of the intermittent feeding, an icon indicative of a number of hours of a duration of the intermittent frequency, an icon indicative of a number of minutes for tapering up each feeding interval, and an icon indicative of a number of minutes for tapering down each feeding interval.

In a further implementation form of the fourth aspect, the method further comprises presenting within the GUI, a graphical timeline indicative of feeding intervals during an upcoming feeding period, wherein solid portions of a first color of the timeline are indicative of time intervals during which entering feeding is taking place, the length of each solid portion of the first color is according to the selected duration, solid portions of a second color of the timeline are indicative of time intervals during which enteral feeding is stopped, the length of each solid portion of the second color is according to the selected frequency less the selected duration, mixed portions that represents a mixture of the first and second colors located before each solid portion of the first color are indicative of taper up and have a length according to the selected taper up time, and mixed portions located after each solid portion of the first color are indicative of taper down and have a length according to the selected taper down time.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3 is a schematic depicting an example of a record of a certain enteral feeding product formulation, in accordance with some embodiments of the present invention;

FIGS. 6A-J include a sequence of exemplary GUI images depicting an exemplary flow for implementing the method of dynamically adjusting an enteral feeding device for controlling the feed rate according to an estimate of the energy expenditure computed based on output of sensors and supplementing the feed formula with extra protein, in accordance with some embodiments of the present invention.

DETAILED DESCRIPTION

Figure 1A:
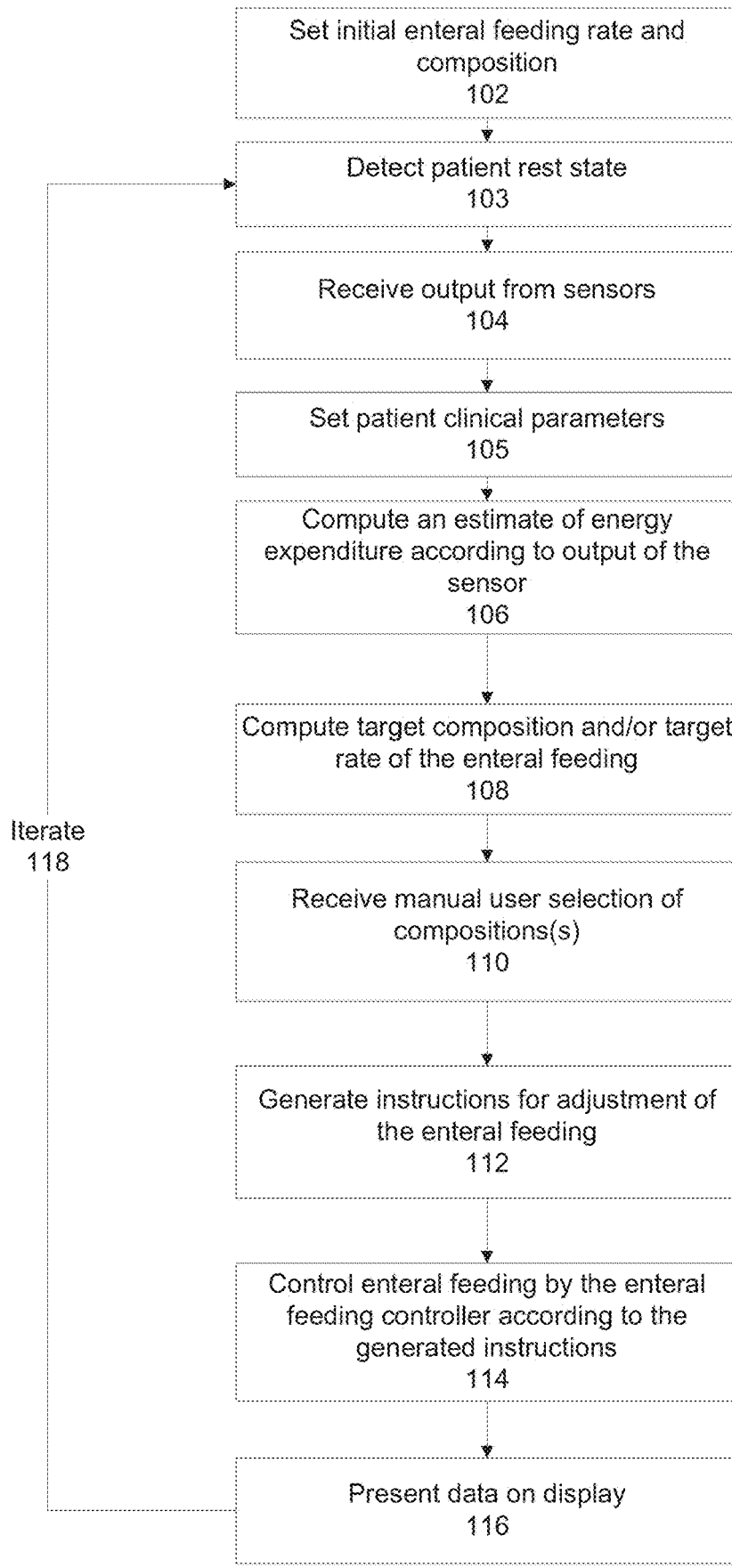
FIG. 1A is a flowchart of a method of dynamically adjusting an enteral feeding device for controlling the enteral feeding rate according to an estimate of energy expenditure computed based on output of sensors, in accordance with some embodiments of the present invention.

The present invention, in some embodiments thereof, relates to enteral feeding systems and, more specifically, but not exclusively, systems and methods for control of enteral feeding.

An aspect of some embodiments of the present invention relates to systems, an apparatus, methods, and/or code instructions (stored in a data storage device, executable by one or more hardware processors) for adjusting the rate of enteral feeding and optionally selecting the type and/or brand of the feeding to be administered for a patient being tube fed by an enteral feeding controller. The rate is adjusted according to a computed estimate of energy expenditure of the patient while maintaining percussions against over feeding that may result undesired reflux. The estimated energy expenditure is computed based on output of one or more sensors such as a carbon dioxide sensor, flow sensor and optionally adding an oxygen sensor that measure inspiration and/or expiration of the patient (e.g., associated with a ventilation device and/or installed), and optionally based on a nitrogen sensor associated with a urine output device or any other means that detects the energy expenditure of the patient. The sensor measurements may be performed in real-time, for example, continuously (and/or substantially continuously when digital signals are outputted at a certain frequency resembling continuous monitoring), or over time intervals for example less than about 5-30 minutes. The estimated energy expenditure may be computed in real-time (i.e., closely following the received sensor measurements) and the rate of enteral feeding adjusted accordingly, in real-time. The feeding rate of the enteral feeding provided to the patient is dynamically adjusted according to the dynamic energy consumption of the patient. As the patient's condition changes (e.g., due to stress, recovery, movement, medication administration, infection), the energy consumption of the patient changes, and is met by the dynamic control of the enteral feeding device.

Optionally, a target composition of the enteral feeding is computed according to the computed estimated energy expenditure. The target composition and/or target feeding rate may be computed according to the nutritional goal of the patient. The computed target composition may be matched by one or more formulations that are actually available used as an initial setting and/or, for example having records stored in a database. When the match is not exact, but represents a similar formulation, the user may select one of the matched records, for example, the most similar formulation that is available in stock. When no matching records are found (i.e., according to the similarity requirement), subsets of components of the target composition may be independently matched as close as possible to formulation required. A different feeding rate may be computed for each matched formulation. A mechanism of the enteral feeding controller controls delivery of each matched formulation according to the respective computed rate.

Optionally, when the target composition and target feeding rate differ from a current enteral feeding composition and feeding rate by a manually defined and/or automatically computed requirement (e.g., percent difference, absolute difference, for example, about 10%) the instructions are generated for adjustment of the rate of delivery of the enteral feeding according to the target composition.

The receiving of the oxygen and/or carbon dioxide measurements and computing of the estimate of energy expenditure are performing iteratively for every first time interval, for example, every 1 minute, 5 minutes, 10 minutes, or other values. The instructions for adjustment are generated (when the requirement is met) for a second time interval that is larger than the first time interval, for example, 30 minutes, 60 minutes, 120 minutes, or other values. The second interval may include multiple time intervals, for example, the instructions are generated based on the previous six first time intervals of five minutes each (e.g., 6×5 minutes=30 minutes. Alternatively or additionally, instructions are generated every second interval, for example, new instructions are generated every 30 minutes (when such new instructions are triggered by significant difference in the energy expenditure of the patient according to the requirement). Effectively, the patient may be monitored for computation of the energy expenditure continuously or close to continuously, with changes to the feeding occurring periodically.

An aspect of some embodiments of the present invention relates to systems, an apparatus, methods, and/or code instructions (stored in a data storage device, executable by one or more hardware processors) for adjusting the rate of enteral feeding for including a protein supplement for obtaining about 100% of a computed target feeding rate of the patient. When the target composition of the enteral feeding is computed, the amount of supplemental protein for adding to available feeding formulations (stored in a database storing records of different formulations) is computed accosting to the target composition. The instructions are generated according to a selection of the available feeding formulations and the amount of supplemental protein (which may be selected according to available supplemental protein formulations).

Inventors observed that in many cases, the calories and proteins of commercially available feeding formulations do not directly match within the tolerance the computed REE. The most common case is lack of sufficient protein within the commercially available feeding formulations to meet patient demands based on REE. When calories computed according to REE are met by the selected feeding formulations, in many cases the protein requirements are not fully met. For example, the commercially available feeding formulation may include 100% of the calories according to the REE, and about 80% of the determined protein requirements.

Optionally, the estimated of the energy expenditure for computation of the target composition is performed when the patient is resting. An analysis of real-time patient vital sign measurements collected from an electronic medical record of the patient may be performed to determine whether the patient is at rest.

The systems, methods, apparatus, and/or code instructions described herein relate to the technical problem of control of enteral feeding of a patient. Design and/or selection of an appropriate enteral feeding regime, which includes the feeding rate (e.g., calories per unit of time) and/or composition of the enteral feeding (e.g., mix of carbohydrates, protein, fat and/or other nutrients) affects patient survival and recovery.

According to standard practice (e.g., when the patient enters the intensive care unit (ICU)) a feeding plan (e.g., formulation, rate, pattern of delivery) is manually assigned, for example, by a healthcare provider and/or nutritionist currently calculating nutritional goal according to Harris Benedict formula or alike (which is generally not accurate and/or performed only one time for the patient) and not according to dynamic- and changing nutritional goal as patient status continuously changes. The feeding plan is selected according to the specific situation of the patient, according to specification(s) of the variations of feedings available from different vendors, and the currently stocked supply. The feeding plan is manually designed based on dietician and/or nutritionist knowhow and/or known recommended formulas, team leader experience (e.g., head of ICU), and/or patient specific requirement as prescribed by the current attending physical. The manual method, which is based on subjective inputs from one or more people, results in sub-optimal planning for the specific patient that does not precisely match the patient's current metabolism.

In contrast to the standard manual practice, the systems, methods, apparatus, and/or code instructions described herein without the need for a "man in the loop" dynamically determine objectively the patient condition in terms of energy expenditure, and dynamically adjust the enteral feeding accordingly.

The systems, methods, apparatus, and/or code instructions described herein may further relate to the technical problem of adjusting patient enteral feeding according to dynamic patient conditions. For example, in the ICU, the patient condition may change rapidly, and many variations may be experienced. For example, as the patient recovers, undergoes changes in treatments, and experiences new infections and new medical conditions. The current practice of manual methods, which are based on manual calculations of the most suitable enteral feeding regime at a certain point in time, are unable to adequately adapt to rapidly changing patient conditions. For example, continuous checking the patient, analyzing the patient condition, replacing different feedings, and updating of the feeding regiment are impractical and cannot be manually performed to keep up with the changing condition of the patient.

When the patient feeding is manually determined and manually performed, the determination of how to feed the patient is based on outdated data which do not reflect the actual current state of the patient. Therefore, the manually determined feeding plan is not suitable for the current state of the patient. In contrast, the systems, methods, and/or code instructions described herein obtain an accurate current state of the patient, and dynamically select and/or adjust the feeding regimen (e.g., composition, rate) for the patient based on the current state of the patient. The feeding regimen is quickly adjusted to reflect changes in the current state of the patient, which cannot be performed by manual methods that are based on outdated states of the patient and not the current state of the patient.

Moreover, healthcare providers are unable to continuously monitor patient caloric consumption, which may lead to sub-optimal feeding of the patient, for example, underfeeding of the patient which may lead to inadequate caloric and/or protein and or nutrition intake with adverse effects on recovery and/or survival, and/or overfeeding (it is noted that overfeeding may be an indication of poor stomach pyloric discharge or other gastric blockage that require special treatment) of the patient which may lead to reflux and associated risks thereof (e.g., aspiration pneumonia).

The systems, methods, apparatus, and/or code instructions described herein do not simply perform automation of a manual procedure, but perform additional automated features which cannot be performed manually by a human using pencil and/or paper. For example, combination of food sources may be controlled each at a respective rate, for example, a high protein food source and a standard food source. In another example, the computations are performed in real-time (i.e., over short intervals) based on sensors measuring oxygen, carbon dioxide, and/or nitrogen flows of the patient, which cannot be performed manually. In yet another example, the target composition and target feeding rate are computed according to the computed energy expenditure and evaluated to determine whether a significant change has occurred from the current feeding. Instructions to adjust the feeding controller are automatically generated when the significant change occurs, to change the composition and/or feeding rate. The process is iterated at short time intervals to quickly identify changes in the energy expenditure of the patient and adjust feeding accordingly, which cannot be performed manually. In yet another example, the feeding is adjusted in real-time to prevent or reduce reflux based on estimated GRV. In another example, a prediction of future feeding needs is made based on historical measurements of feeding performance.

The GUI associated with the systems, apparatus, methods and/or code instructions described herein generates a new user experience, one that is different than manually trying to select feeding formulas and select the feeding rate. For example, the GUI guides the user through the process of selecting the feeding formulas and the feeding rate, as described herein. The GUI visually presents different suitable and available feeding formulas for the user to pick from. The GUI guides the user to select supplemental protein from suitable and available feeding formula. The GUI presents to the user suitable options based on the automatically computed resting energy expenditure of the patient, which aids the user in making correct feeding selections. The GUI may present a graphical representation of selected intermittent feeding parameters, to help visualize how the feeding will take placing during the upcoming time interval.

The systems, methods, and/or code instructions described herein do not simply display information using a GUI. The systems, methods, and/or code instructions described herein may be based on a specific, structured GUI, which is paired with a prescribed functionality directly related to the GUI's structure that is addressed to and resolves the specifically identified technical problem.

When the features related to by the systems, methods, apparatus, and/or code instructions described herein are taken as a whole, the combination of the features amounts to significantly more than a simple mathematical calculation of computing the estimated energy expenditure rate (e.g., the resting energy expenditure rate). The systems, methods, apparatus, and/or code instructions described herein do not merely relate to mathematical computations (e.g., equations), but relate to the particular data collected, stored, and the way the data is collected by sensors, and how instructions for adjustment of the enteral feeding device (e.g., pump, valve) are automatically generated.

The systems, methods, apparatus, and/or code instructions described herein improve an underlying technical process within the technical field of enteral feeding systems, in particular within the field of automated control of patient enteral feeding.

The systems, methods, apparatus, and/or code instructions described herein provide a unique, particular, and advanced technique of dynamically determining the energy expenditure of the enteral fed patient, and generating instructions for dynamically adjusting an enteral feeding device (e.g., pump, valve) delivering the enteral feeding according to the determined energy expenditure, optionally to match (or minimize the difference, for example, within a tolerance) the enteral feeding to the energy expenditure.

The systems, methods, apparatus, and/or code instructions described herein are tied to physical real-life components, for example, one or more of: sensor(s) that measure oxygen, carbon dioxide, and nitrogen, computational hardware (e.g., hardware processor(s), physical memory device) that analyzes the sensor output, and an enteral feeding device that controls the enteral feeding into the patient.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term energy expenditure may sometimes be interchanged with the term resting energy expenditure. The terms energy expenditure and resting energy expenditure, as used herein, refer to the indigenous un-intervened energy also known as resting energy (e.g., calorie) requirements of the monitored patient.

As used herein, the term enteral feeding may sometimes be interchanged with the term tube feeding. The terms enteral feeding and tube feeding, as used herein, refer to feeding of the patient via a tube inserted into the stomach of the patient. The tube is inserted into the stomach (or duodenum, or jejunum, or other locations in the digestive track) via the nose, the mouth, or a surgically created opening.

Figure 1B:
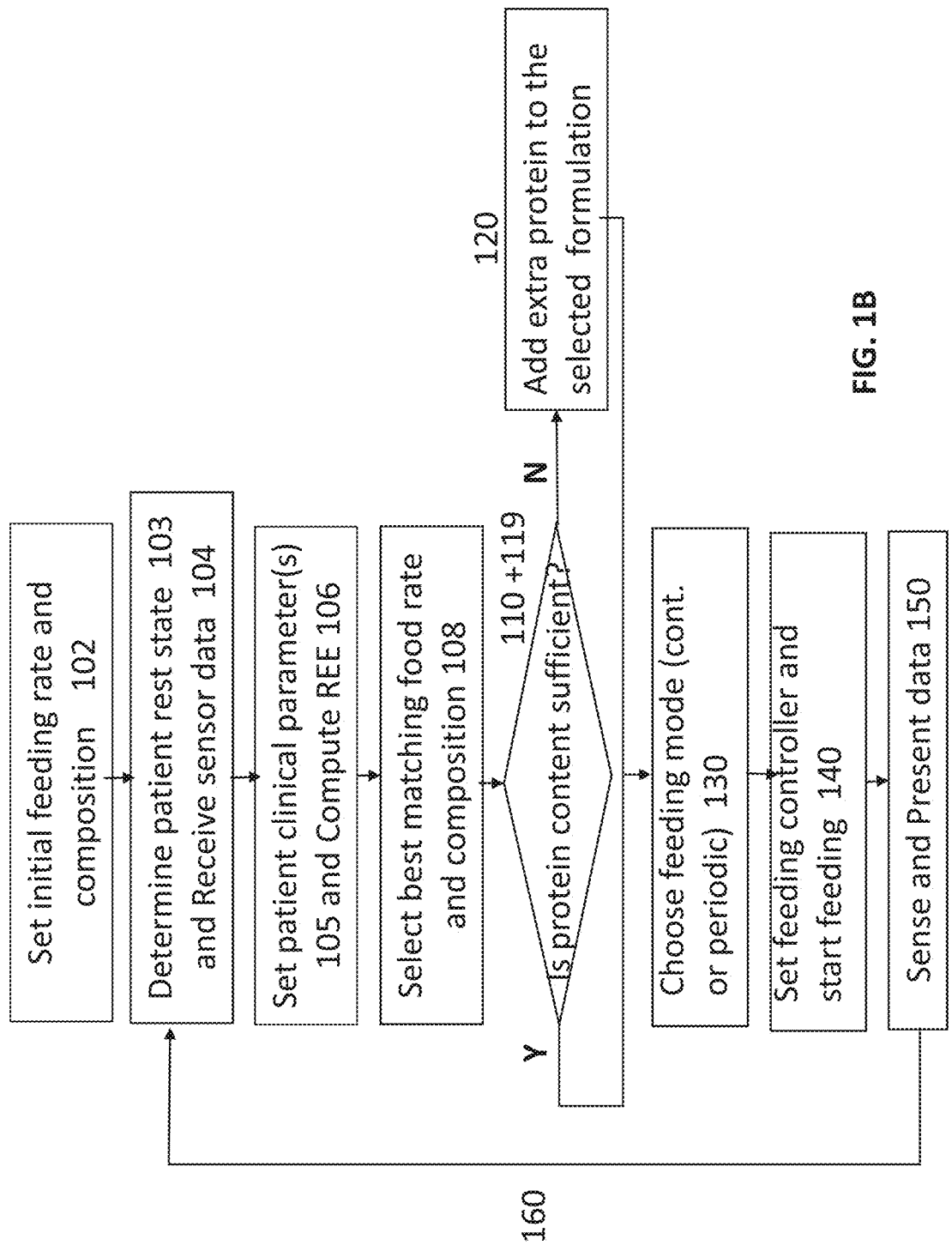
FIG. 1B is a flowchart of a method of dynamically adjusting an enteral feeding device for controlling the feed rate according to an estimate of the energy expenditure computed based on output of sensors and supplementing the feed formula with extra protein, in accordance with some embodiments of the present invention.

Reference is now made to FIG. 1A, which is a flowchart of a method of dynamically adjusting an enteral feeding controller that controls the enteral feeding rate according to an estimate of energy expenditure computed based on output of sensors, in accordance with some embodiments of the present invention. Reference is also made to FIG. 1B, which is a flowchart of a modified method of dynamically adjusting an enteral feeding device for controlling the feed rate according to an estimate of the energy expenditure computed based on output of sensors and supplementing the feed formula with extra protein, in accordance with some embodiments of the present invention. The protein may be supplemented according to the level recommended by the care taker (i.e., user), and/or automatically selected by code. A continuous feeding regimen or intermittent feeding regimen may be automatically selected by code, and/or manually selected by the care taker (i.e., user).

If vital signs indicate that the patient is not in resting status the additional implementation of the method is to be halted until the patient is determined to be in the resting state. Monitoring of the patient may continue to determine when the patient enters the resting state.

Figure 2:
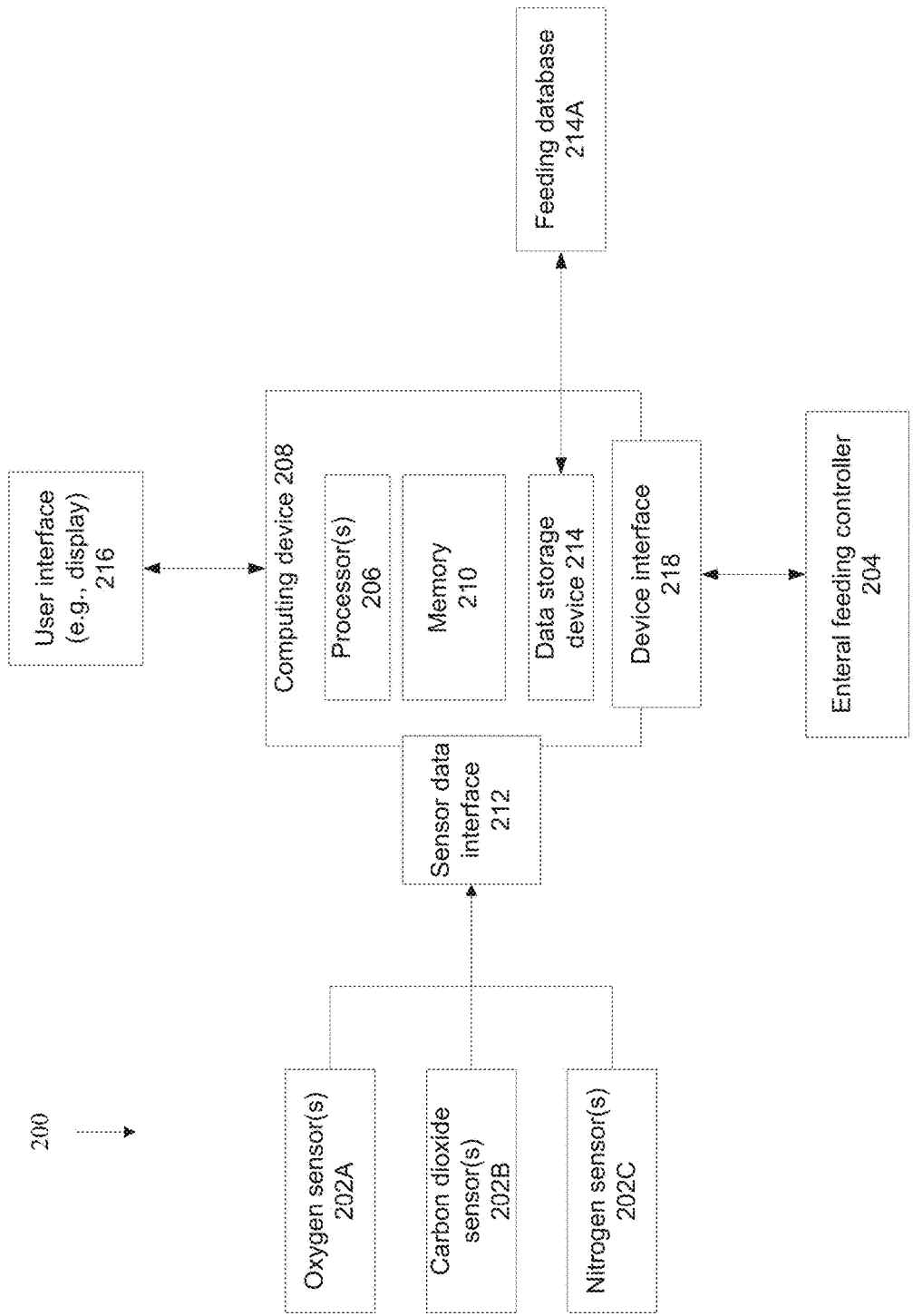
FIG. 2 is a schematic of components of a system for estimating energy expenditure based on output of sensors, and generating instructions for adjustment of the enteral feeding rate provided by an enteral feeding controller according to the estimated energy expenditure, in accordance with some embodiments of the present invention.

Reference is also made to FIG. 2, which is a schematic of components of a system 200 for estimating energy expenditure based on output of one or more sensors 202A-C, and generating instructions for adjustment of the enteral feeding rate provided by an enteral feeding controller 204 according to the estimated energy expenditure, in accordance with some embodiments of the present invention. One or more acts of the method described with reference to FIGS. 1A and/or 1B may be implemented by components of system 200, as described herein, for example, by a processor(s) 206 of a computing device 208 executing code instructions stored in a memory (also referred to as a program store) 210 (other vital signals for example blood saturation and other analytes may be incorporated into the calculations).

Computing device 208 receives electrical signals outputted by one or more oxygen sensors 202A, and/or one or more carbon dioxide sensors 202B. Computing device 208 may receive electrical signals outputted by one or more nitrogen sensors 202C. Oxygen sensor(s) 202A and/or carbon dioxide sensor(s) 202B measure inspiration and/or expiration of the patient (e.g., that occur naturally by respiration of the patient and/or occur by an external device forcefully ventilating the patient). Sensors 202A-B may be, for example, located within a ventilation device that provides oxygen to the patient, for example, within a ventilation tube (e.g., endotracheal tube) in a mechanically ventilated patient, within a Venturi mask and/or nasal cannula on a patient breathing on their own, and/or within components of the mechanical ventilation machine and/or components associated with the Venturi mask. Nitrogen sensor(s) 202C may be located, for example, within a urinary catheter, within a urine collection bag, and/or within other urine flow devices and/or urine collection devices (and optionally other vital signals for example blood saturation may be incorporated into the calculations).

Computing device 208 may receive the outputs of one or more sensors 202A-C via one or more sensor interfaces 212, for example, a network interface, a wire connection, a wireless connection, a local bus, other physical interface implementations, and/or virtual interfaces (e.g., software interface, application programming interface (API), software development kit (SDK)).

Computing device 208 may be implemented as, for example, a standalone unit, a client terminal, a server, a computing cloud, a mobile device, a desktop computer, a thin client, a Smartphone, a Tablet computer, a laptop computer, a wearable computer, glasses computer, and a watch computer. Computing device 208 may be implemented as a customized unit that include locally stored software and/or hardware that perform one or more of the acts described with reference to FIGS. 1A and/or 1B. Alternatively or additionally, computing device 208 may be implemented as code instructions loaded on an existing computing device. Alternatively or additionally, computing device 208 may be implemented as hardware and/or code instructions (e.g., an accelerator card) installed and/or integrated within an existing computing device.

Processor(s) 206 of computing device 208 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 206 may include one or more processors (homogenous or heterogeneous), which may be arranged for parallel processing, as clusters and/or as one or more multi core processing units.

Memory (also known herein as a data storage device) 210 stores code instructions executable by processor(s) 206, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 210 stores code instruction that implement one or more acts of the method described with reference to FIGS. 1A and/or 1B. Alternatively or additionally, one or more acts of the method described with reference to FIGS. 1A and/or 1B are implemented in hardware.

Computing device 208 may include a data storage device 214 for storing data, for example, feeding database 214A that stores records of composition of enteral feeding formulations, for example, from different vendors. Data storage device 214 may be implemented as, for example, a memory, a local hard-drive, a removable storage unit, an optical disk, a storage device, and/or as a remote server and/or computing cloud (e.g., accessed via a network connection).

Computing device 208 includes and/or is in communication with a user interface 216 that includes a mechanism for a user to enter data (e.g., patient information, initial enteral feeding rate and/or composition) and/or view presented data (e.g., computed energy expenditure, changes to the enteral feeding rate and/or changes to the composition of the enteral feeding). Exemplary user interfaces 216 include, for example, one or more of, a touchscreen, a display, a keyboard, a mouse, and voice activated software using speakers and microphone. External devices communicating with computing device 208 may serve as user interfaces 216, for example, a smartphone running an application may establish communication (e.g., cellular, network, short range wireless) with computing device 208 using a communication interface (e.g., network interface, cellular interface, short range wireless network interface). The user may enter data and/or view data on the display of the smartphone, optionally via a graphical user interface (GUI) application.

Computing device 208 includes a device interface 218 that provides electrical communication with an enteral feeding controller 204 that controls enteral feeding of the patient via an enteral feeding tube. Enteral feeding controller 204 controls and/or adjusts the rate of the enteral feeding according to instructions generated by computing device 208 in response to the estimated energy expenditure computed based on output of sensor(s) 202A-B and optionally sensor 202C. Enteral feeding controller 204 (and/or another device) may adjust the composition of the enteral feeding according to instructions generated by computing device 208. Device interface 218 may be implemented as, for example, a network interface card, a hardware interface card, a wireless interface, a physical interface for connecting to a cable, a virtual interface implemented in software, communication software providing higher layers of connectivity, and/or other implementations. Enteral feeding controller 204 may be implemented using a mechanical based mechanism, and/using computer components (e.g., processor(s), memory storing code instructions executable by the processor(s), and/or hardware components). Enteral feeding controller 204 may be implemented as a pump (e.g., positive displacement feed pump) that is controlled to deliver enteral feedings to the patient via the enteral feeding tube according to the rate defined by the instructions generated by computing device 208. Enteral feeding controller 204 may include a valve that selectively opens the lumen of the enteral feeding tube so that enteral feeding may be delivered to the patient at the defined rate.

Enteral feeding controller 204 may include a feeding selecting mechanism that controls delivery of multiple formulations, each at a defined rate. For example, a valve that selects between two tubes, each providing a different formulation at a respective different feeding rate, according to the generated instructions. It is noted that an increase of the protein percentage in the feeding formula may be manually selected by the user and/or automatically selected by code as shown schematically with reference to FIG. 1B.

Referring now back to FIG. 1A, at 102, an initial enteral feeding rate and/or initial enteral feeding composition is set. The initial enteral feeding rate and/or initial enteral feeding composition may be entered into computing device 208, for example, manually by the user via user interface 216, for example, via a graphical user interface (GUI) presented on a display, automatically computed based on one or more values manually entered and/or automatically obtained from storage (e.g., from an electronic health record). For example, the basal metabolic rate, which may be used to set the initial estimated energy expenditure and/or corresponding initial feeding rate and/or initial feeding composition, may be computed according to the Harris-Benedict equation. The initial enteral feeding rate and/or initial enteral feeding composition may be based on a manual subjective observation of the current status of the patient and/or according to available feeding materials (e.g., stock). The initial enteral feeding composition may be selected, for example, based on body parameters (e.g., weight, height, age) according to current practice (e.g., ICU best practices).

The initial enteral feeding rate and/or initial enteral feeding composition is dynamically adjusted, as described herein with reference to acts 104-116. The adjustment may be performed continuously, triggered based on detected events, and/or at predefined time intervals. The adjustment is performed in real time, without a significant and/or detectable delay.

Optionally, a mismatch between the computed estimate of energy expenditure (as described with reference to act 106) and the initial state is computed. The instructions for adjusting the initial state of the enteral feeding controller 204 are generated according to the computed mismatch (as described with reference to act 112).

Optionally, at 103, an analysis is performed to determine whether the patient is at rest. Optionally, the resting energy expenditure is computed (as described herein) when the patient is determined to be at rest. When the patient is not at rest, the initial programmed and/or manually determined patient feeding setting may be continued, as described with reference to act 102.

The determination of whether the patient is resting or not may be determined, for example, by a set-of-rules applied to patient data. For example, an analysis of data obtained from patient monitoring sensors (and/or devices) and/or obtained from an electronic health record may be made to determine whether the patient is at rest. The electronic medical and/or health record of the patient may be accessed by computing device 208 via a network interface, for example via HL7 protocol. Computing device 208 may receive patient data, optionally patient vital sign measurements, optionally in real-time and/or near real-time (e.g., within about 1 minute, 5 minutes, 10 minutes, or other values). Exemplary patient data that is analyzed to determine rest (or not) includes one or more of: heart rate, blood pressure, oxygen saturation (e.g., measured manually by nurses, and/or automatically by a device such as a pulse oximetry and/or sphygmomanometer). For example, a patient with a baseline normal heart rate experiencing tachycardia (fast heart rate), for example, due to stimulation (e.g., medical procedure being performed, stress), may not be considered at rest.

When the patient is not at rest, the patient data may be monitored (e.g., continuously and/or at short intervals, for example, every 5, 10, 15 minutes or other values) to determine whether the patient entered the rest state. Alternatively, when the patient is determined to be resting, the patient data may be monitored to determine whether the patient is still resting or entered a non-rest state.

When the patient is determined to not be at rest, an alert may be generated indicative of the lack of rest state of the patient, for example, as a message displayed on the GUI.

At 104, an oxygen measurement outputted by an oxygen sensor(s) 202A and a carbon dioxide measurement outputted by a carbon dioxide sensor(s) 202B associated with a ventilation device (e.g., ventilation tube, mask) of the patient is received by computing device 208, optionally via sensor interface 212.

Oxygen and/or carbon dioxide measurements are performed on inspired air and/or expired air.

The net oxygen flow rate (i.e., into the patient) and the net carbon dioxide flow rate (i.e., out of the patient) may be computed. The net oxygen and carbon dioxide flow rates are indicative of indirect calorimetry, based on the oxidation balance of carbohydrates (e.g., glucose), fat, and/or protein, by the body of the patient.

Some embodiment(s) relate to performing the feed rate and composition calculations based on exhaled $CO_2$ sensing exclusively.

Optionally, a urine nitrogen measurement outputted by a nitrogen sensor(s) 202C is received by computing device 208. The indirect calorimeter computation (i.e., the estimate of energy expenditure) is dynamically computed according to the nitrogen measurement, as described herein. The urine nitrogen measurement is indicative of protein oxidation. The urine nitrogen measurement increased the precision of the computed estimated energy expenditure as an indirect calorimetry indication. Alternatively, the urine nitrogen may be computed as an approximation, without measuring the nitrogen in the urine by the nitrogen sensor.

In terms of mathematical representation:
$\dot{V}O_2$ denotes the net flow of oxygen (e.g., liters per min (L/min))
$\dot{V}CO_2$ denotes the net flow of carbon dioxide (e.g., liters per min (L/min))
$\dot{N}$ denotes the net amount of nitrogen (e.g., gram per min (L/min))

$$\bar{m} = \begin{bmatrix} \dot{V}CO2 \\ \dot{V}O2 \end{bmatrix} \begin{matrix} \text{Denotes a measurement vector,} \\ \text{CO2, O2 in [L/min]} \end{matrix}$$

$$\bar{m} = \begin{bmatrix} \dot{V}CO2 \\ \dot{V}O2 \\ \dot{N} \end{bmatrix} \begin{matrix} \text{Denotes the measurement vector,} \\ \text{CO2, O2 in [L/min] and nitrogen} \\ \text{[gram/min]} \end{matrix}$$

Optionally, at 105, one or more clinical parameters of the patient are set. The clinical parameters may be manually entered by a user (e.g., via the GUI), automatically computed (e.g., based on sensor data and/or other data obtained for example from the electronic health record of the patient) and/or retrieved from a data storage device (e.g. from the electronic health record of the patient).

The clinical state of the patient may be received. The clinical state of the patient may include one or more medical diagnoses of the patient. The clinical state of the patient may affect computation of the target feeding composition. Exemplary clinical states include: maintenance, stressed/MICU, trauma/general surgery, trauma/ICU, burn(s), cancer, obesity (e.g., body mass index (BMI)>29.9).

The weight of the patient may be received. The weight of the patient may affect computation of the target feeding composition.

Patients with different clinical states and/or different weights may have different nutritional goals, which may affect computation of the target composition and/or target feeding rate.

At 106, an estimate of energy expenditure of the patient is dynamically computed based on the oxygen measurement, the carbon dioxide measurement, and optionally the nitrogen measurement. The estimate of energy expenditure is dynamically computed as a rate of energy expenditure for a predefined time duration during which the oxygen and carbon dioxide measurements are obtained, for example, over about a minute, 5 minutes, 15 minutes, 30 minutes, 1 hour, or other time intervals. Alternatively, when intermittent feeding is selected (as described herein), the estimate of energy expenditure may be dynamically computed during the intermittent feeding intervals. Energy expenditure may not necessarily be computed during between the intermittent feeding intervals when no feeding is occurring.

It should be noted that the calculations are leading to needed composition of the feeding material and are not necessarily limited to flow rate only.

Energy expenditure denotes an accurate indicator for intake of food requirements of patients, in particular patients in an ICU (or similar) setting. The estimate of energy expenditure represents an estimate of caloric expenditure of the patient. The estimate of energy expenditure is computed based on metabolic rate estimated from oxygen consumption computed based on the oxygen measurement, and carbon dioxide production computed based on the carbon dioxide measurement. As discussed herein, the enteral feeding controller dynamically adjusts the enteral feeding rate to deliver calories to the patient, to replenish the caloric expenditure according to the computed estimate.

Since as discussed herein, the energy expenditure of the enteral fed patient may be assumed to be resting energy expenditure, the estimate of the energy expenditure (i.e., resting energy expenditure (REE)) may be computed according to the Weir equation (or other corresponding and/or similar methods), mathematically represented as follows:

$$REE\left[\frac{kJ}{day}\right] = [16.2, 5, -6] \cdot \overline{m}$$

$$REE\left[\frac{kJ}{day}\right] = 16.2 \cdot \dot{V}O2 + 5 \cdot \dot{V}CO2 - 6 \cdot \dot{N}$$

When oxygen measurements are not available (e.g., no oxygen sensor is installed, the oxygen sensor fails), the REE may be calculated based on the carbon dioxide measurement and an assumed and/or estimated value for respiratory quotient (RQ), for example, 0.85. Alternatively, when oxygen measurements are available, RQ may be calculated, and food composition may be adjusted accordingly.

Optionally, a prediction of future energy expenditures is computed based on current and/or historical sensor measurements. The prediction may be based on, for example, detection of similar previously observed patterns. For example, the patient may experience different energy expenditures at different times of the day, such as during the day and during the night. The prediction may be performed based on detected patterns, for example, detection of an onset of the nighttime pattern indicative of relatively lower energy expenditure for an upcoming period of time. The prediction may be computed, for example, by machine learning code instructions (e.g., neural network) that is trained on historical sensor measurements (and optionally corresponding computed energy expenditures) and performs prediction.

At 108, a target composition and/or rate of the enteral feeding is computed. The target composition and/or target rate denotes the best matching food rate and/or composition for the patient. Optionally, an adjustment of the existing enteral feeding composition and/or initial set rate to arrive at the target composition and/or target rate is computed. As the patient's condition changes (e.g., due to stress, recovery, movement, medication administration, infection), the ideal composition requirements for the patient change, and are met by the dynamic computation of the target feeding composition and/or target rate for which a similar available feeding formulate is selected.

Optionally, the target composition and/or feeding rate is evaluated relative to the current enteral feeding composition and/or feeding rate according to a requirement, for example, an absolute difference and/or relative difference (e.g., over 5%, or 10%, or 20%, or over 10 cc/hour, or 25 cc/hour, or over 100 calories, or over 150 calories, or other values). When the requirement is not met, no change to the target composition and/or feeding rate is necessarily required. The energy expenditure may be re-computed at a future point in time to determine when the requirement is met.

Optionally, the target composition and/or target feeding rate includes an amount of water, which may be added separately to an available powder composition and/or powder protein composition. The ratio between the amounts of water to be added to a certain amount of powder may be computed, optionally according to the ratio of water to powder currently being delivered and/or recently provided.

The target composition and/or rate of the enteral feeding may be computed in view of the patient clinical condition and/or patient weight (e.g., as described with reference to act 105).

The target composition and/or rate of the enteral feeding may be computed according to the nutritional goal of the patient.

The target rate of delivery of the enteral feeding is computed according to the estimate of energy expenditure in view of the target feeding composition.

The enteral feeding delivery rate that is controlled by the enteral feeding device may be mathematically represented as, where cc denotes cubic centimeters, and hr denotes per hour:

$$\dot{f} \ [cc/hr]$$

The target composition of the enteral feeding is computed according to the computed estimate of energy expenditure. The target composition may include defined amounts (e.g., weight, percentage) of glucose (denoted $\dot{g}$), lipids (denoted $\dot{l}$), and/or protein (denoted $\dot{p}$). The target composition may be represented as a feeding vector, which may be mathematically represented as:

$$\dot{f} = \begin{bmatrix} \dot{g} \\ \dot{l} \\ \dot{p} \end{bmatrix}$$

The feeding vector (i.e., composition, for example, glucose, lipids, and/or protein), may be computed based on the computed estimate of energy expenditure, and/or indirect calorimetry vector $\overline{m}$, for example, as described by Eric Jequier, Kevin Acheson, and Yves Shutz, "*Assessment of Energy Expenditure and Fuel Utilization in Man*", Ann. Rev. Nutr. 1987. 7:187-208.

It should be made clear that the equations presented herein are exemplary and not necessarily limiting. It is noted that future research may recommend modification of the described equations and/or suggest new equations. The systems, apparatus, methods, and/or code instructions described herein implement such new and/or modified equations by the controller.

The target composition may be computed in accordance for reaching a nutritional goal of the patient. The nutritional goal may be determined, for example, based on an aggregation of data collected from multiple sampled individuals, based on clinical evidence, based on expert opinion stored in a database, optionally based on machine learning methods that the analyze patient data and/or the clinical evidence and/or the expert opinion. Optionally, the target composition is computed based on an aggregation of data collected from multiple sampled individuals. The target composition may be computed according to a probability of obtaining the best outcome (e.g., recovery, improved survival). For example, different compositions fed to different patients, and the experienced outcomes (e.g., recovery, improved survival, death, discharge, re-admittance). The target composition may be computed, for example, by machine learning code instructions (e.g., neural network) that is trained on data of multiple other patients (e.g., provided composition, outcome) and computes the composition most likely to lead to the best outcome (e.g., recover, improved survival). Optionally, feeding database 214A is searched to identify one or more records of available feeding formulations according to the computed target composition (e.g., the feeding vector). Optionally, when no exact matching record is available, the closest matching records are found. The closest matching records may be ranked according a similarity requirement to the target composition. The closest matching records may be computed, for example, based on a least square fit, based on a best fit parameter, a correlation parameter, a computed statistical distance, or other measurements of similarity requirement that indicate similarity between datasets (e.g., vector distance).

Optionally, when no available matching records are found (i.e., according to the similarity requirement), components of the computed target composition may be matched independently and/or in sets to records of feeding database 214A. For example, for a certain patient, a pure protein component of the target composition may be computed, for example, as described in additional detail with reference to FIG. 1B. When no available matching record is found that includes pure protein, the other components may be matched to a certain formulation record, and the pure protein may be matched to another record (for example, provided as an adviser to the treating physician and will depend on his/her decision).

Feeding database 214A may be locally stored on computing device 208, and/or remotely stored (e.g., on a data storage device, network server, computing cloud) and accessed for example over a network.

Reference is now made to FIG. 3, which is a schematic depicting an example of a record of a certain enteral feeding product formulation, in accordance with some embodiments of the present invention. Data for the formation depicted in FIG. 3 is stored as a record in feeding database 214A. The formulation depicted in FIG. 3 may be selected and/or ranked for a similar computed target composition, according to the similarity requirement.

The identified matching records of feeding formulations may be presented on a display, for example, within a GUI. Optionally, a ranking score indicative of the similarity between the matching record and the target composition is presented. The identified matching records may or may not be physically available in stock. The presentation of multiple records that are the most similar to the target composition enables the user to choose the formulation that is actually available in stock.

Optionally, a change in composition of the feeding formulation is automatically suggested. The change may be suggested when the newly computed target composition is significantly different from the current feeding formulation being provided (e.g., which may have been previously selected by the user), for example, according to a similarity requirement. One or more suggested newly computed target compositions may be presented to the user on the display, for example, within the GUI.

Referring now back to FIG. 1A, at 110, the user may manually select the feeding composition(s) to feed the patient from the list of matching records that represent the closest compositions to the computed target composition. For example, the user may manually click within the GUI presented on the display to select the feeding composition.

Optionally, a mismatch is identified between a currently computed available feeding composition and a previously computed available feeding composition. The mismatch may be corrected by computing the additional feeding composition (e.g., as described with reference to FIG. 1B) for providing the currently computed available feeding composition.

The selected composition may be obtained and connected to enteral feeding controller 204. The feeding tube may be primed and prepared to deliver the selected composition to the patient.

Alternatively, the selection of the composition may be automatically performed by computing device 208. The selected composition may be automatically connected to enteral feeding controller 204. The user may be asked to verify the automated selection, for example, by clicking OK on a display. The automatic connection of the selected feeding composition may be performed, for example, by a robotic system that automatically retrieves the selected composition and connects the selected composition, or for example, multiple compositions may be pre-set with the final connection to the enteral feeding controller performed automatically by a connection mechanism.

Optionally, additional additives are added to the selected feeding materials. The additional additives may be manually added by the user, and/or automatically inserted by an automated system (e.g., robot). The additional additives include materials not defined by the target composition. For example, when the target composition includes glucose, fat, and protein, the additional additives may include nutrients (e.g., vitamins, minerals), fiber, and/or other substances.

Alternatively or additionally, when no nitrogen measurement is available (and/or when a user manually selects to ignore the nitrogen measurements), an enhanced protein diet may be added to the target composition. The enhanced protein diet may be selected based on research evidence showing benefit in reducing mortality. For example, about 1.2-2.0 gram (gm) of protein per kilogram (Kg) of body weight, for example, about 1.5 gr/Kg. The protein may be considered as an additive, since nitrogen measurement values are not considered in computing the target composition. The target composition may be computed based on caloric demand.

At 112, instructions for adjustment of the feeding rate by enteral feeding controller 204 are automatically generated by computing device 208. The adjustment may be provided, for example, as a new feeding rate, or a change from the existing feeding rate.

It is noted that computing device 208 may be integrated with enteral feeding controller, or computing device 208 may exist as an independent device that transmits the generated instructions to enteral feeding controller 204.

The rate of delivery of the enteral feeding, when different from the computed target feeding rate, may be adjusted accordingly. For example, when the selected feeding composition is different than the target feeding composition, the actual rate of delivery may be adjusted accordingly.

Optionally, another set of instructions is generated. The second set of instructions may be integrated with the first set of instructions (e.g., provided to a common controller), and/or the first and second instructions may be outputted to two independent controllers (which may synchronize with one another). The second set of instructions may define adjustment of the rate of the second component(s) of the selected enteral feeding formulation, for example, the pure protein component discussed herein with reference to act 108 and/or as described with reference to FIG. 1B. It is noted that three or more sets of instructions may be generated according to the number of independently matched sets of components. Each instruction set defines the rate of delivery of the respective components of the enteral formulation, for example, independent rates for each of glucose, fat, protein, and/or other nutrients.

Optionally, the instructions for dynamic adjustment of the enteral feeding by the enteral feeding controller are set below a reflux generating feeding level (e.g., threshold, range) estimated to trigger reflux of the enteral feeding by the patient. Controlling to feeding rate to remain below the reflux feeding level may prevent or reduce reflux of the enteral feedings by the patient, which may reduce or prevent related complications such as aspiration pneumonia. The reflux feeding level may be computed according to the net food portion of an estimated gastro residual volume (GRV). The estimate of the GRV may be computed, for example, based on weight, volume, and specific gravity of the enteral feeding delivered by the enteral feeding pump. One method of making decisions regarding enteral feeding involves manually measuring the volume of digestive contents in the patient's stomach after an enteral feeding session, by using a syringe to aspirate the stomach contents. The measured volume is termed Gastric Residual Volume (GRV). The value of the GRV is used by healthcare professional to decide, for example, if the patient received enough food, is having problems ingesting the delivered food, and/or if the patient is at increased risk of aspiration pneumonia. For example, when the measured GRV is above a threshold, the next enteral feeding is delayed. A full assessment using GRV may take up to 72 hours, with 4 hour intervals between GRV measurements. Computing the estimate of the GRV as described herein may reduce or prevent procedures for direct measurement of the GRV, for example, according to common practice: withdrawing the contents of the stomach, measuring the volume of the withdrawn contents, and returning the withdrawn contents back into the stomach.

The GRV measured may be used for modification of the feed rate according to:

$$V_f(\text{modified}) = V_f - \frac{W_{GRV}}{\rho_{GRV} \cdot \Delta t}$$

Where WGRV denotes the weight of the collected GRV, Vf denotes the volume of the enteral formulation, $\rho_{GRV}$ denotes the specific gravity of the collected GRV, and $\Delta t$ denotes the accumulation period, for example 1 hour.

The energy consumption based computed rate of the enteral feeding may be manually and/or automatically reduced accordingly in view of the computed GRV and threshold. The target composition may be adjusted accordingly, for example, to compensate for the adjusted in the rate. For example, the reduction in rate to avoid reflux may reduce the protein the patient requires. The target composition may be adjusted to include additional protein to make up for the potential loss of protein at the reduced rate.

Optionally, the feeding rate is personalized based on historical feeding performance. The personalization may be performed, for example, based on historical data indicating that the patient is able to handle a feeding rate without reflux, which is 75% below the reflux threshold otherwise computed. The personalization may be based on, for example, an analysis of positive and/or negative feeding performance. For example, the patient may reflux at different reflux thresholds at different times of the day, such as during the day and during the night. The personalization may be computed, for example, by machine learning code instructions (e.g., neural network) that is trained on historical feeding performance (e.g., feeding rates, indications of reflux or no reflux) and performs the personalization.

At 114, enteral feeding controller 204 implements the received instructions, and controls delivery of the selected enteral composition according to the computed rate.

Optionally, in the case of receiving the two sets of instructions (e.g., the separate sets, and/or the combined sets), the two sets of instructions are implemented by enteral feeding controller 204. For example, the two sets of instructions may be implemented by alternating delivery of the two compositions, each at a respective rate (i.e., sequential delivery). In another example, the two sets of instructions may be implemented in parallel, for example, delivering two compositions each at a respective rate.

Optionally, the first and second set of generated instructions control a feed selecting mechanism (e.g., pinch valve) that selects between a first tube that delivers the enteral feeding (or other selected set of component(s)) and a second tube that delivers the protein component (or other set of component(s)). The first tube and the second tube may connect into a combined tube that provides the enteral feeding of the patient, or each tube may independently provide the enteral feeding (i.e., without the combined tube).

Figure 4:
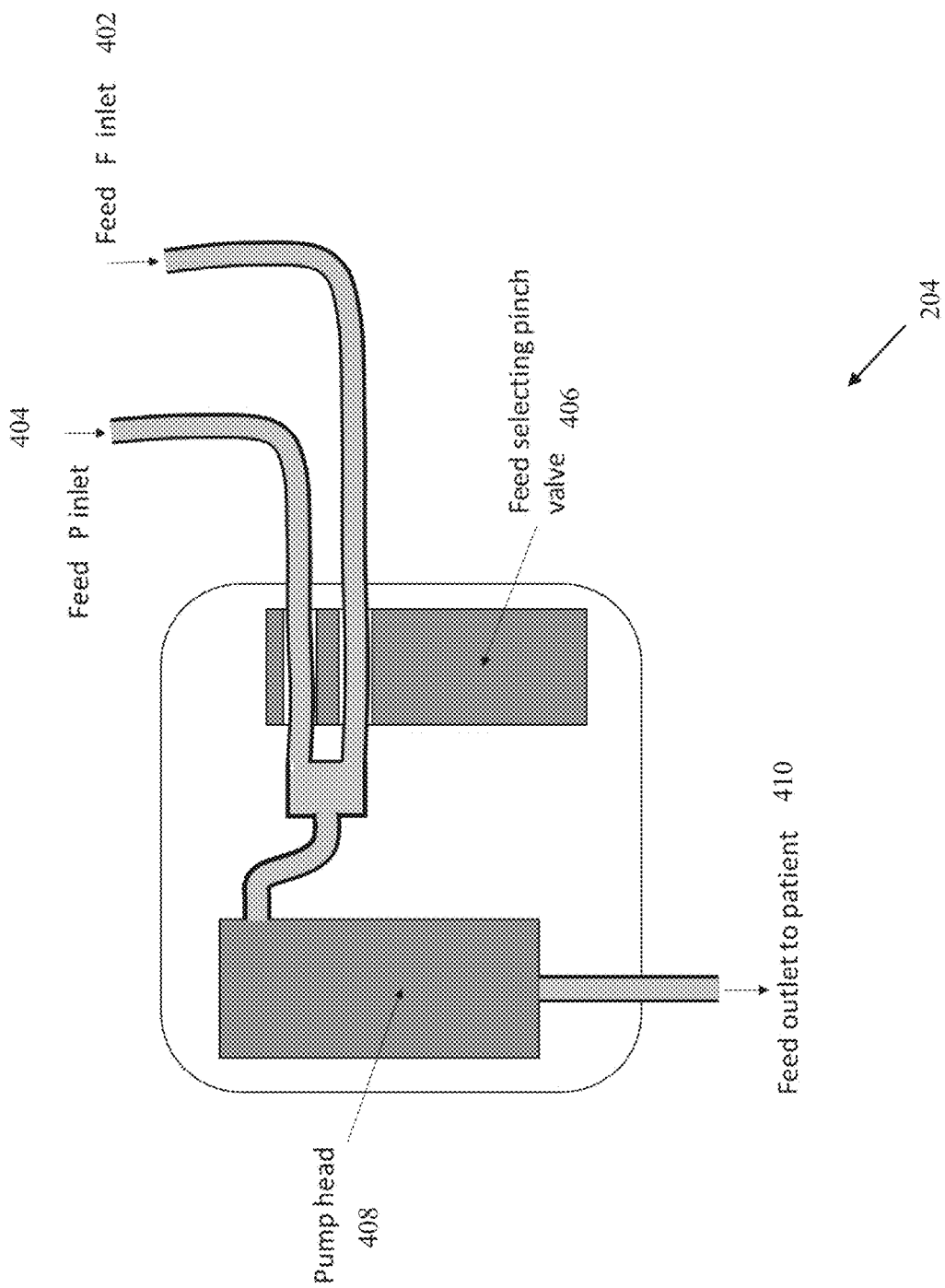
FIG. 4 is a schematic of an exemplary implementation of the enteral feeding device for independent control of the rate of delivery of two components of the enteral feeding, in accordance with some embodiments of the present invention.

Reference is now made to FIG. 4, which is a schematic of an exemplary implementation of the enteral feeding device (e.g., 204 of FIG. 2) for independent control of the rate of delivery of two components of the enteral feeding, in accordance with some embodiments of the present invention. Enteral feeding device 204 includes one standard feed inlet 402 of a first tube F through which the standard selected enteral feeding composition is provided (i.e., a first set of components), and another feed inlet 404 of a second tube P through which the selected protein supplement (i.e. a second set of components) is provided, in accordance with some embodiments of the present invention. A feed selecting pinch valve 406 (or other implementation of a selection switch) controls which of the two tubes F and P supplies its respective contents to pump head 408 for delivery to the patient via tube outlet 410. Feed selecting pinch valve 406 alternatively switches between protein tube P and standard feeding tube F to obtain the selected composition, which is delivered to the patient by pump 408.

At 116, data is presented on a display (e.g., user interface 216), optionally within a graphical user interface (GUI). The presented data may be dynamically updated accordingly.

Exemplary data presented on the display include one or more of:
Current computed estimated energy expenditure, for example, as a numerical value.
A trend based on history of the computed energy expenditure, for example, presented as a graph denoting a trend line plotting based on previously computed points indicative of estimated energy expenditures.
Current feeding rate delivered by the enteral feeding pump.
Computed target composition, selected formulation, and similarity between the target composition and the selected formulation.

The presented data may be saved in a log, database, and/or other data structure, for example, stored in data storage device 214 and/or another storage device. The stored data may be analyzed off-line, for example, a meta-analysis of feeding effectiveness may be computed based on data collected from multiple patients.

At 118, one or more features described with reference to acts 104-116 are iterated. The iterations are performed to dynamically adjust the enteral feeding rate according to dynamics of the current energy expenditure of the patient.

The iterations may be performed, for example, continuously (e.g., when sensor measurements are analogue signals) or near continuously (e.g., when digital sampling is performed), at predefined time intervals (e.g., one minute between iterations, or other values, for example, less than about 5, 10, 15, 30, 60 minutes, or other time intervals between iterations), and/or at triggers (e.g., detection of an increase in heart rate, manual selection by a user, administration of medication).

Optionally, the sensor measurements and the computation of the energy expenditure are performed iteratively according to a first rate and/or first time interval, for example, to perform continuous and/or near continuous real time monitoring, for example, less than about 5, 10, 15, 30, 60 minutes, or other time intervals. The instructions for adjustment of the enteral feeding may be iterated at a second time interval that is larger than the first time interval, for example, at least every 30 minutes, 60 minutes, 120 minutes or other values. In this manner, the patient may be continuously monitored for changes in energy expenditure, while the actual formula and/or rate changes occur less frequently.

Optionally, the feeding rate provided by the enteral feeding pump is dynamically adjusted to match the rate of energy expenditure within a tolerance requirement. The enteral feeding pump may perform local monitoring and/or control over the actual delivered feeding rate, to maintain the instructed feeding rate within the tolerance requirement. For example, a closed loop may include local sensors to measure the actual delivered feeding rate and a valve to adjust the actual feeding rate accordingly.

The iterations correct the difference (e.g., error) between the initial settings of the feeding rate and/or composition (e.g., as described with reference to act 102) and the actual patient requirements estimated by the computed energy expenditure and/or corresponding computed composition. Equilibrium may be reached between the estimated energy expenditure and the provided enteral feeding (i.e., rate and/or composition) as the difference is reduced.

Referring now back to FIG. 1B, acts 102-110 are as described with reference to FIG. 1A.

At 119, an analysis is performed (e.g., by code instructions stored in memory 210 executed by hardware processor(s) 206 of computing device 208) to determine whether the calories and protein of the selected composition (which may match the target composition, or may represent the closest available match to the target composition, as described herein) match within a tolerance to the computed REE of the patient.

At 120, supplemental protein is added to the selected feeding formulation when the protein content of the selected feeding formulation is determined to be insufficient for meeting patient needs computed based on the REE.

When protein provided by the selected feeding formulation is determined to be insufficient, the amount of supplemental protein to meet patient requirements is computed.

It is noted that the supplemental protein may be added without significantly increasing the caloric and/or volumetric feeding rate computed for the selected composition. The selected composition may not necessarily require re-computation and/or re-selection in view of the computed supplemental protein. For example, supplemental protein may be added as a powder mixed into the liquid selected feeding composition. Alternatively, the feeding rate of the supplemental protein is independently computed and delivered, as described herein.

The amount of supplemental protein may be presented on the GUI and/or stored in memory for further processing. Commercially available protein supplements (e.g., that are currently available in stock) may be presented on the GUI, and/or stored in memory for further processing.

Supplemental protein may be added as follows:

Manually by a user. The GUI may present the computed REE and/or supplemental protein requirements. The user may view the list of available protein supplements, and make a manual selection. The user may mix the protein supplement within the selected feeding composition, and/or connect the selected protein supplement to the dual feeding pump, as described herein (e.g., with reference to FIG. 4).

Semi-automatically by the user and code. Based on the computed REE, the target feeding composition, and available feeding formulations, code instructions may compute the closest matching available feeding formulation as described herein. The amount of supplemental protein is computed according to available protein supplements (e.g., stored in a database). The code instructions may compute options of the closest matching protein supplements according to availability (e.g., stored in a database). The GUI may present the available options for user selection. The user selects the protein supplement and connects the selected feeding composition and protein supplement.

Fully automatic. Based on the computed REE, the target composition, and available formulations, code instructions may compute the closest matching available formulation as described herein. The code instructions may compute the amount and/or type of supplemental protein that when added to the selected composition arrives at the protein required by the patient (i.e., to obtain 100% of the patient requirements). The amount and/or type of supplemental protein is computed according to available protein supplements (e.g., stored in a database). The GUI may present instructions to the user to attach the selected formulation and selected protein supplement to the pump, or to mix the protein supplement and selected formulation (e.g., add protein powder into the liquid formulation).

At 130, the feeding mode is selected. Feeding may be may be continuous, for example, a constant rate throughout the day (e.g., over 24 hours). Alternatively, feeding may be intermittent, for example, 1 hour feeding intervals followed by 5 hours of no feeding, repeated 4 times a day. Such intermittent feeding may let the gastric system of the patient rest between consecutive feedings (e.g., more similar to normal eating of meals separated by no-eating intervals). The continuous and/or intermittent feeding may be variable and/or incremental (e.g., based on a function and/or set-of-rules), for example, initially set at 50% of patient feeding requirements, and rising to 100% of the patient feeding requirements over a predefined time period (e.g., 3 days). The incremental rise may be linear, exponential, or using other implementations.

The continuous or intermittent and optionally incremented feeding may be selected, for example, with reference to feeding loop 302 described with reference to FIG. 5, and/or act 114 and/or 118 described with reference to FIG. 1A.

At 140, the feeding controller is set and the selected feeding composition and supplemental protein is delivered.

At 150, the actual feeding is monitored and/or data is presented on the display, as described with reference to act 116 of FIG. 1A.

At 160, one or more features described with reference to acts 104-150 are iterated. The iterations are performed to dynamically adjust the enteral feeding rate and/or the selected formulation and/or the supplemental protein according to dynamics of the current resting energy expenditure of the patient.

Figure 5:
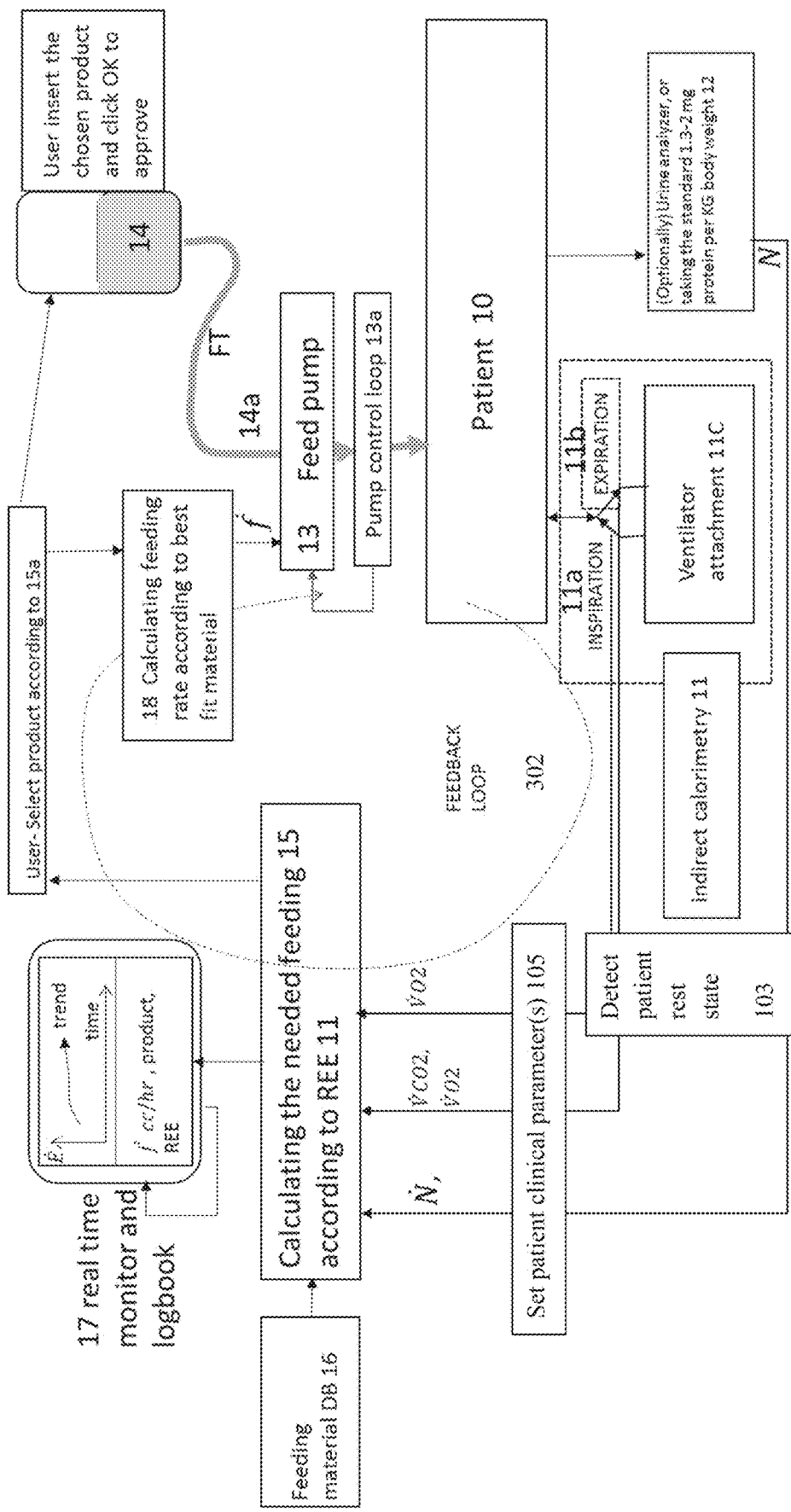
FIG. 5 is a dataflow diagram of dynamic adjustment of an enteral feeding rate by an enteral feeding controller according to an estimated energy expenditure computed based on output of sensor(s), in accordance with some embodiments of the present invention.

Reference is now made to FIG. 5, which is a dataflow diagram of dynamic adjustment of an enteral feeding rate by an enteral feeding controller according to an estimated energy expenditure computed based on output of sensor(s), in accordance with some embodiments of the present invention. The dataflow diagram described with reference to FIG. 5 depicts dataflow based on the method described with reference to FIGS. 1A-B, and/or within an implementation based on components of system 200 described with reference to FIG. 2. The dataflow diagram described with reference to FIG. 5 depicts a closed feedback loop 302, which adjusts the enteral feeding rate and/or compositions according to changes in patient condition detected based on sensor measurements.

Patient 10 denotes a mechanically ventilated and enteral fed patient (e.g., in the ICU). Indirect calorimetry 11 is performed to estimate the energy expenditure of patient 10, to determine the enteral feeding for meeting the calorie expenditure of patient 10. Patient 10 is ventilated via a ventilator attachment 11C. Oxygen and carbon dioxide sensors measure oxygen consumption and carbon dioxide production during patient 10 inspiration 11a and expiration 11b via ventilator attachment 11c.

Optionally, at 12, nitrogen output is measured by a urine sensor and/or estimated, for example, according to an estimated value of 1.3-2 milligrams of protein produced per kilogram of body weight.

Optionally, at 103, the patient rest state is computed as described with reference to act 103 of FIG. 1A. When the patient is at rest, the feedback loop 302 continues. When the patient is not at rest, the feedback loop 302 is halted until the patient is determined to be at rest.

Optionally, at 105, clinical parameter(s) of the patient are set as described with reference to act 105 of FIG. 1A.

At 15, the enteral feeding rate is calculated according to the estimated energy expenditure (optionally the resting energy expenditure) 11, which is computed based on the measured oxygen consumption, carbon dioxide production, and nitrogen production. At 16, the composition of the enteral feeding may be selected according to a database of available feeding materials. Multiple enteral feeding products may be presented for use selection, optionally according to a ranking. The ranking may denote a measure of similarity to the computed idea enteral feeding composition. The enteral feeding rate and/or composition of the enteral feeding may be computed according to the clinical parameter(s) of the patient.

Optionally, at 17, a display may present real time monitoring data, which may be stored in a logbook. The real time monitoring data may be presented as a graph depicting trends over time in the computed estimated energy expenditure and/or the computed enteral feeding rate. The real time monitoring data may include the current and/or instantaneous numerical value of the computed energy expenditure and/or feeding rate, for example, in cubic centimeters (cc) per hour.

Optionally, at 15a, a user (e.g., healthcare worker) selects one or more enteral feeding products from the computed set of available enteral products which may be used to obtain a composition that is similar to the ideal computed composition. Optionally, when protein content of the available enteral products is insufficient, and supplemental protein is required, the supplemental protein formulation may be selected as described with reference to acts 119 and/or 120 of FIG. 1B.

At 14, the user inserts the selected enteral feeding product and/or supplemental protein product into the enteral feeding system and clicks OK to approve the selection. The user may select the feeding mode as described with reference to act 130 of FIG. 1B.

At 14a the feeding tube is primed. At 18, the feeding rate is calculated according to the best fit between the user selected enteral feeding product and the ideal feeding rate of the ideal enteral feeding formulation.

At 13, the feeding pump delivers the user selected feeding product(s) to patient 10 via the feeding tube, according to the computed feeding rate. At 13a, a pump control loop executed by the feeding pump may monitored the delivered enteral feeding, and adjust the actual feeding rate according to the computed feeding rate.

Feedback loop 302 is iterated, to dynamically compute the estimated energy expenditure and corresponding feeding rate, as described herein.

Reference is now made to FIGS. 6A-J, which is a sequence of exemplary GUI images depicting an exemplary flow for implementing the method of dynamically adjusting an enteral feeding device for controlling the feed rate according to an estimate of the energy expenditure computed based on output of sensors and supplementing the feed formula with extra protein (e.g., as described with reference to FIGS. 1A-B), in accordance with some embodiments of the present invention.

Figure 6A:
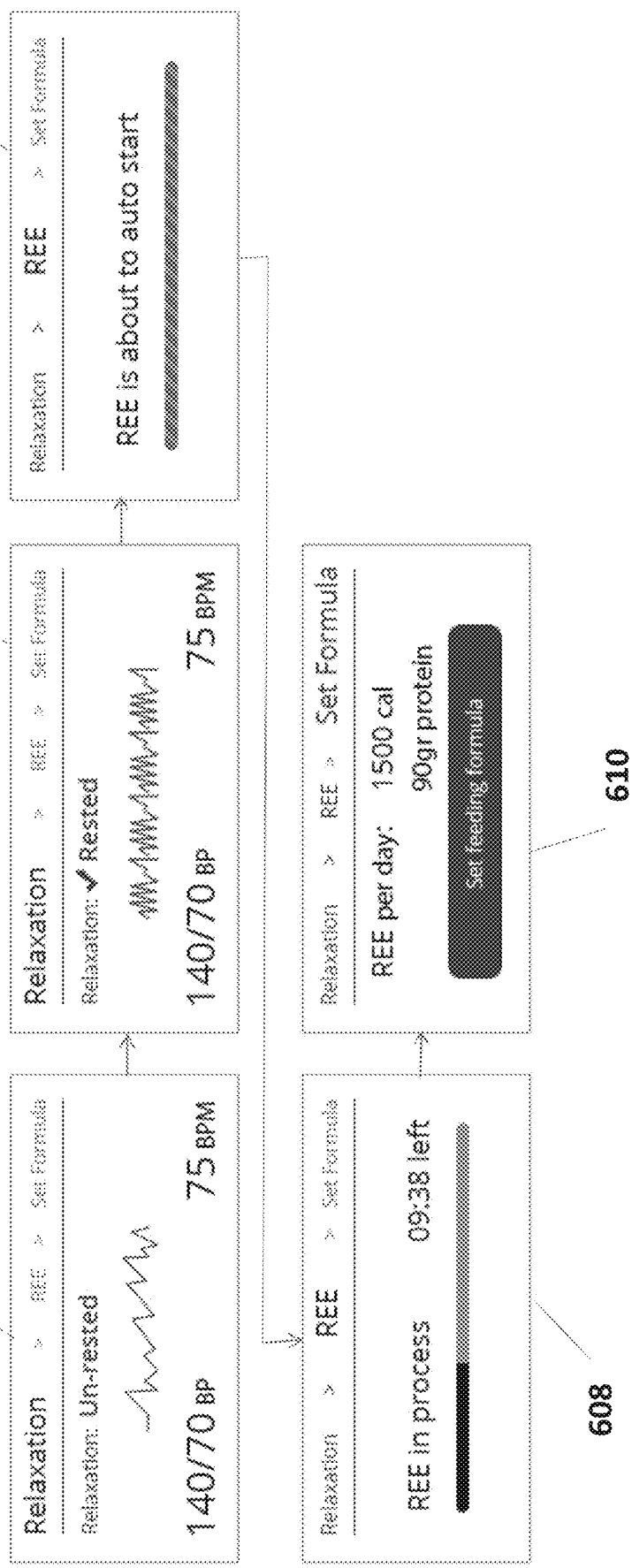

FIG. 6A depicts a sequence of GUI images for determining the patient rest state based on an analysis of patient vital signs, for example, as described with reference to feature 103 of FIGS. 1A-1B. GUI 602 depicts that the patient is determined to be not at rest (i.e., unstable). GUI 604 depicts that the patient is determined to be at rest. An initial feeding rate and composition is set when the patient is determined to be at rest, for example, as described with reference to feature 102 of FIGS. 1A-1B. GUI 606 depicts that the REE computation is starting. GUI 608 depicts computation of the REE over a time interval. GUI 610 depicts the resulting computed REE, shown as 1440 and 60 cc (cubic centimeter)/hour.

FIG. 6B depicts a GUI image for setting clinical parameters of the patient, including patient weight 612 and selecting from one or more of the following conditions 614: maintenance, stressed/MICU, Trauma/General Surgery, Trauma/ICU, Burns, Cancer, and Obesity, for example, as described with reference to feature 105 of FIGS. 1A-1B. The REE is automatically computed based on the set clinical parameters, for example, as described with reference to feature 106 of FIGS. 1A-1B.

In the depicted example, the patient weight 612 is set to 50 Kg, and no conditions 614 are selected. The REE 616 is computed as 1500, and 60 cc/hour.

FIG. 6C depicts another setting of the GUI described with reference to FIG. 6B for another patient. In the depicted example, the patient weight 612 is set to 85 Kg, and the condition 614 Trauma/ICU is selected. The REE 616 is computed as 1800, and 75 cc/hour.

FIG. 6D depicts a GUI image that presents the best formula available that is closest to the computed target composition and/or target rate, i.e., optimal formula 618, for example, as described with reference to feature 108 of FIGS. 1A-1B. In the depicted example, the Optimal Formula Osmolite is selected, which includes 100% of the computed calories and 85% of the protein based on the REE, at a rate of 75 cc/hour, for example, as described with reference to feature 110 of FIGS. 1A-1B. The formula is selected for continuous feeding. It is noted that the optimal formulas are selected to provide 100% of the computed required calories (or near 100%) irrespective of the protein requirements. The optimal formulas are selected based on the assumption that the remaining required protein will be met by adding a supplemental protein formulation.

FIG. 6E depicts a GUI image that is presented when an analysis determines that the protein content of the selected optimal formula Osmolite is insufficient, for example, as described with reference to feature 119 of FIG. 1B. A list of supplemental protein formulas are presented within the GUI for selection for addition to the selected optimal formula Osmolite, for example, as described with reference to feature 120 of FIG. 1B. The list of supplemental protein formulas and recommended amounts are automatically computed, for example, as described with reference to the paragraph "Semi-automatically" with reference to feature 120 of FIG. 1B.

FIG. 6F depicts a GUI image of a selection of 45 grams of the supplemental formula Gold Standard 100% for addition to the optimal formula Osmolite, for example, as described with reference to feature 120 of FIG. 1B. FIG. 6G depicts a GUI image of a manual selection 620 of the type of formula and a manual selection of the quantity, for example, as described with reference to feature 110 of FIGS. 1A-1B, and/or as described with reference to the paragraph "Manually by a user" with reference to feature 120 of FIG. 1B. In the depicted example, the user manually selected to feed Osmolite at a rate of 75 cc/hour.

It is noted that the average feeding formula denoting available formulas that are closes to the target composition, without supplemental protein being added. Such average feeding formulas provide the closest possible calories and proteins to the patient.

FIG. 6H depicts the GUI image described with reference to FIG. 6G that includes a data entry field 622 for manually selecting the quantity for feeding (i.e., other than the amounts available by clicking on the presented quantity icons).

FIG. 6I depicts a GUI image for manually defining parameters of an intermittent feeding. Exemplary intermittent feeding parameters that may be set include:

Frequency, for example, 2 hours, 3 hours, 4 hours, and 6 hours.

Duration, for example, 1 hour, 2 hours.

Taper up, for example, 5 minutes, 10 minutes, 15 minutes, and 20 minutes.

Taper down, for example, 5 minutes, 10 minutes, 15 minutes, and 20 minutes.

For example, as described with reference to feature 130 of FIG. 1B.

Figure 6J:
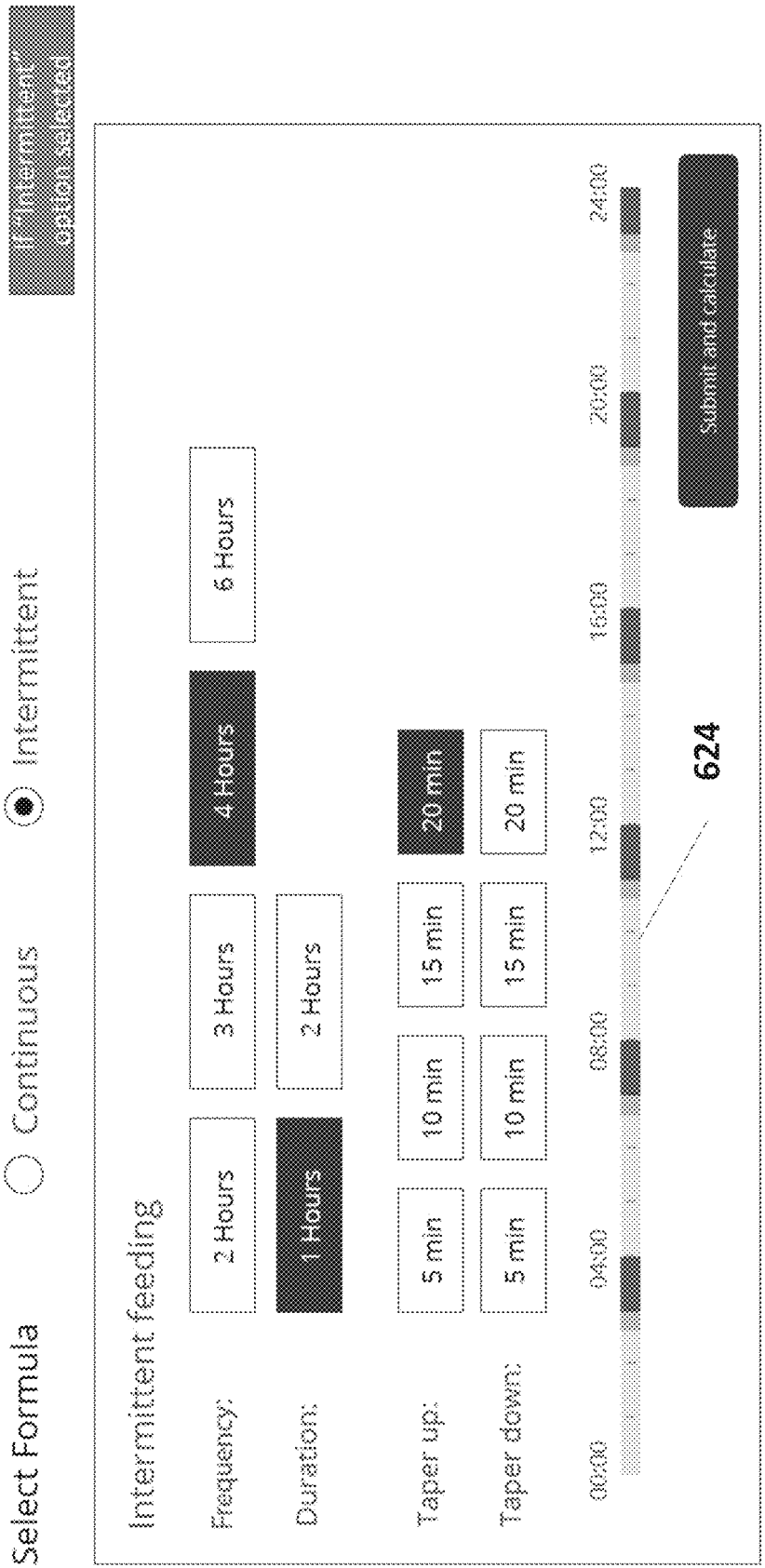

FIG. 6J depicts the GUI image described with reference to FIG. 6I, in which the following parameters are selected: Frequency of 4 hours, duration of 1 hour, taper up of 20 minutes. A timeline 624 may graphically depict the feeding pattern during a 24 interval according to the selected parameters. For example, solid portions of a first color of the timeline are indicative of time intervals during which entering feeding is taking place, the length of each solid portion of the first color is according to the selected duration, solid portions of a second color of the timeline are indicative of time intervals during which enteral feeding is stopped, the length of each solid portion of the second color is according to the selected frequency less the selected duration, mixed portions that represents a mixture of the first and second colors located before each solid portion of the first color are indicative of taper up and have a length according to the selected taper up time, and mixed portions located after each solid portion of the first color are indicative of taper down and have a length according to the selected taper down time.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant enteral feeding controllers will be developed and the scope of the term enteral feeding controller is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer-implemented method of adjusting enteral feeding of a patient by an enteral feeding controller, comprising:
   receiving output of a carbon dioxide sensor that senses at least one of inspiration and expiration of the patient;
   receiving output of a flow sensor that senses at least one of inspiration and expiration of the patient;
   computing energy expenditure of the patient based on the output of the carbon dioxide sensor and the flow sensor;
   computing a target nutritional goal for the enteral feeding that provides 100% or near 100% of the computed energy expenditure of the patient irrespective of a predictive equation;
   selecting a target feeding formula from a plurality of feeding formulas according to the target nutritional goal;
   generating instructions for adjustment, by an enteral feeding controller, for delivery of the target feeding formula; and
   providing the generated instructions to the enteral feeding controller to deliver enteral feedings to the patient via an enteral feeding tube from at least one feed inlet of at least one feeding tube according to at least one of a feeding rate and a feeding composition defined by the generated instructions.

2. The method of claim 1, further comprising performing an analysis of real-time patient vial sign measurements collected from an electronic medical record of the patient to determine whether the patient is at rest, wherein the energy expenditure of the patient is computed when the patient is determined to be at rest.

3. The method of claim 1, wherein the instructions for adjustment include a first feeding interval associated with the rate of delivery of the target feeding formula, and second non-feeding interval during which no enteral feeding is delivered, wherein the first and second intervals are iterated.

4. The method of claim 1, wherein the target nutritional goal is calculated based on output of the carbon dioxide sensor alone when output of the flow sensor is not available, and an estimated value for a respiratory quotient (RQ).

5. The method of claim 1, further comprising receiving a nitrogen measurement outputted by a nitrogen sensor associated with a urine output collection device that collects urine outputted by the patient, and wherein the energy expenditure is further computed according to the nitrogen measurement.

6. The method of claim 1, further comprising computing an amount of supplemental protein to meet enteral feeding requirements of the patient based on the computed energy expenditure, wherein the amount of supplemental protein is computed based on the target feeding formula in view of available formulation stored in a database storing records of different feeding formulas of enteral feeding formulation, wherein the supplemental protein when added to a selected available formulation does not significantly affect a computed caloric and/or volumetric feed rate of the available formulation to trigger a re-computation of the feeding rate of the available formulation.

7. The method of claim 1, further comprising:
   matching the computed target nutritional goal to at least one record of an available feeding formula stored in a database storing records of different feeding formulas, wherein the instructions for adjustment are generated based on the matched at least one record.

8. The method of claim 1, wherein when at least one record is matched to the target nutritional goal, further comprising presenting on a display the at least one record, and receiving via a user interface a selection of a certain record from the presented at least one record, wherein the instructions for adjustment are generated according to the selected certain record.

9. The method according to claim 8, further comprising computing a score indicative of similarity between each respective record and the target nutritional goal, and presenting the score in association with each respective record, wherein when no records are matched to the target nutritional goal, further comprising independently matching a plurality of component sets of the target nutritional goalto respective a plurality of records, wherein each of a plurality of instructions for adjustment is generated according to a respective matched record of the plurality of records, and wherein a first set of components denotes arbitrary components matched to a first formulation, and a second set of components denotes a pure protein component matched to a second formulation, wherein a first set of instructions is generated for enteral feeding of the first formulation at a first rate, and a second set of instructions is generated for enteral feeding of the second formulation at a second rate.

10. The method of claim 1, wherein the target feeding formula is computed based on an aggregation of data collected from a plurality of sampled individuals, wherein the target feeding formula is computed according to a likelihood of obtaining a positive outcome.

11. The method of claim 1, wherein the generated instructions include a first set of instructions for delivery of a first enteral feeding formulation at a first rate, and a second set of instructions for delivery of a second enteral feeding formulation at a second rate, wherein the first set of instructions and the second set of instructions control a feed selecting mechanism that selects between a first tube that delivers the first enteral feeding formulation at the first rate and a second tube that delivers the second enteral feeding formulation at the second rate, wherein the first tube and the second tube connect into a combined tube that provides enteral feeding of the patient.

12. The method of claim 1, wherein the energy expenditure is dynamically computed as a rate of energy expenditure for a predefined time duration during which the output of the carbon dioxide sensor and the flow sensor are obtained, and wherein the feeding rate provided by the enteral feeding controller is dynamically adjusted to match the rate of energy expenditure within a tolerance requirement.

13. The method of claim 1, wherein the generated instructions define a feeding rate set below a reflux feeding level estimated to trigger reflux of the enteral feeding by the patient, computed based on collected gastro residual volume (GRV).

14. The method of claim 1, wherein a feeding rate for delivery of the target feeding formula defined by the instructions is further adjusted based a collected gastro residual volume (GRV), and based on weight, and volume of the selected target feeding formula delivered by the enteral feeding controller.

15. The method of claim 1, wherein the energy expenditure is computed based on a Weir or corresponding equations, and based on metabolic rate estimated from oxygen consumption computed based on output of the flow sensor and carbon dioxide production computed based on output of the carbon dioxide sensor.

16. The method of claim 1, further comprising:
   setting an initial feeding rate by the enteral feeding controller independently of the output of the carbon dioxide sensor and the flow sensor;
   computing a mismatch between the computed energy expenditure and the initial feeding rate state;
   wherein the generated instructions include instructions for adjusting the initial feeding rate of the enteral feeding controller according to the computed mismatch.

17. The method of claim 1, wherein the energy expenditure comprises a prediction of future energy expenditure computed by machine learning code instructions trained according to previously observed patterns.

18. The method of claim 1, wherein the rate of delivery of the target feeding formula is further computed according to historical feeding performance of the patient indications.

19. A system for adjusting enteral feeding of a patient by an enteral feeding controller, comprising:
   a non-transitory memory having stored there a code for execution by at least one hardware processor of a computing system, the code comprising:
      code for receiving output of a carbon dioxide sensor that senses at least one of inspiration and expiration of the patient;
      code for receiving output of a flow sensor that senses at least one of inspiration and expiration of the patient;
      code for computing energy expenditure of the patient based on the output of the carbon dioxide sensor and the flow sensor;
      code for computing a target nutritional goal for the enteral feeding that provides 100% or near 100% of the computed energy expenditure of the patient irrespective of a predictive equation;
      code for selecting a target feeding formula from a plurality of feeding formulas according to the target nutritional goal;
      code for generating instructions for adjustment, by an enteral feeding controller, for delivery of the target feeding formula; and
      code for providing the generated instructions to the enteral feeding controller via a communication interface coupled to said at least one hardware processor to deliver enteral feedings to the patient via an enteral feeding tube from at least one feed inlet of at least one feeding tube according to at least one of a feeding rate and a feeding composition defined by the generated instructions.

20. A computer program product for adjusting enteral feeding of a patient by an enteral feeding controller, comprising:
   a non-transitory memory having stored there a code for execution by at least one hardware processor of a computing system, the code comprising:
      instructions for receiving output of a carbon dioxide sensor that senses at least one of inspiration and expiration of the patient;
      instructions for receiving output of a flow sensor that senses at least one of inspiration and expiration of the patient;
      instructions for computing energy expenditure of the patient based on the flow measurement and the carbon dioxide measurement;
      instructions for computing a target nutritional goal for the enteral feeding that provides 100% or near 100% of the computed energy expenditure of the patient irrespective of a predictive equation;
      instructions for selecting a target feeding formula from a plurality of feeding formulas according to the target nutritional goal;
      instructions for generating instructions for adjustment, by an enteral feeding controller, for delivery of the target feeding formula; and
      instructions for providing the generated instructions to the enteral feeding controller via a communication interface coupled to said at least one hardware processor to deliver enteral feedings to the patient via an enteral feeding tube from at least one feed inlet of at least one feeding tube according to at least one of a feeding rate and a feeding composition defined by the generated instructions.

21. The method of claim 1, further comprising receiving output of an oxygen sensor that senses at least one of inspiration and expiration of the patient, wherein the energy expenditure is computed based on the flow measurement, the carbon dioxide measurement and the oxygen measurement.

* * * * *